US012746206B2

(12) United States Patent
Durham et al.

(10) Patent No.: US 12,746,206 B2
(45) Date of Patent: Sep. 29, 2026

(54) API STABILITY IN SOFTGELS

(71) Applicant: R.P. SCHERER TECHNOLOGIES, LLC, Carson City, NV (US)

(72) Inventors: Douglas Keith Durham, Windsor (CA); Hitesh S. Patel, Windsor (CA)

(73) Assignee: R.P. Scherer Technologies, LLC, Carson City, NV (US)

(*) Notice: Subject to any disclaimer, the term of this patent is extended or adjusted under 35 U.S.C. 154(b) by 1066 days.

(21) Appl. No.: 17/438,335

(22) PCT Filed: Mar. 11, 2020

(86) PCT No.: PCT/US2020/022114
§ 371 (c)(1),
(2) Date: Sep. 10, 2021

(87) PCT Pub. No.: WO2020/185904
PCT Pub. Date: Sep. 17, 2020

(65) Prior Publication Data

US 2022/0175683 A1 Jun. 9, 2022

Related U.S. Application Data

(60) Provisional application No. 62/816,621, filed on Mar. 11, 2019.

(51) Int. Cl.

| | |
|---|---|
| ***A61K 9/48*** | (2006.01) |
| ***A61K 31/09*** | (2006.01) |
| ***A61K 31/137*** | (2006.01) |
| ***A61K 31/167*** | (2006.01) |
| ***A61K 31/192*** | (2006.01) |
| ***A61K 31/485*** | (2006.01) |

(52) U.S. Cl.
CPC ............ *A61K 9/4866* (2013.01); *A61K 9/485* (2013.01); *A61K 9/4858* (2013.01); *A61K 31/09* (2013.01); *A61K 31/137* (2013.01); *A61K 31/167* (2013.01); *A61K 31/192* (2013.01); *A61K 31/485* (2013.01)

(58) Field of Classification Search
CPC .. A61K 2300/00; A61K 31/09; A61K 31/137; A61K 31/167; A61K 31/192; A61K 31/485; A61K 47/10; A61K 47/32; A61K 9/485; A61K 9/4858; A61K 9/4866; A61K 31/138
See application file for complete search history.

(56) References Cited

U.S. PATENT DOCUMENTS

| | | | | |
|---|---|---|---|---|
| 4,522,828 | A * | 6/1985 | Jeffery | A61P 25/24 514/408 |
| 5,141,961 | A | 8/1992 | Coapman | |
| 2008/0014274 | A1 | 1/2008 | Bubnis et al. | |
| 2014/0243364 | A1 | 8/2014 | Agisim et al. | |

FOREIGN PATENT DOCUMENTS

| | | | |
|---|---|---|---|
| CN | 105007891 | A | 10/2015 |
| JP | H03-005418 | A | 1/1991 |
| JP | H03-5418 | U | 1/1991 |
| JP | H10-167988 | A | 6/1998 |
| JP | 2016-510019 | A | 4/2016 |
| KR | 10-2015-0111358 | A | 10/2015 |
| WO | 97/02273 | A1 | 1/1997 |
| WO | 2014/132163 | A1 | 9/2014 |
| WO | 2016/084099 | A1 | 6/2016 |

OTHER PUBLICATIONS

BASF Kollidon 30 Product Briefer; 2 pages; downloaded Jan. 27, 2025.*
Winkler; Natural Science; 2015, 7, pp. 548-557. Published Nov. 24, 2015.*
Winkle, Rudolf; "Iodine—A Potential Antioxidant and the Role of Iodine/Iodide in Health and Disease"; Natural Science, vol. 7, No. 12; pp. 548-557. Published Nov. 2015 (Year: 2015).*
Office Action dated Apr. 14, 2024, directed to IL Application No. 286239; 3 pages.
Office Action dated Jul. 6, 2024, directed to BR Application No. 112021017876-7; 5 pages.
Office Action dated May 13, 2024, directed to JP Application No. 2021-554781; 5 pages.
Office Action dated May 17, 2024, directed to CO Application No. NC2021/0012391; 12 pages.
Office Action dated May 6, 2024, directed to MX Application No. MX/a/2021/010959; 7 pages.
Office Action dated Dec. 1, 2023, directed to CA Application No. 3, 134,031; 3 pages.
Office Action dated Dec. 18, 2023, directed to JP Application No. 2021-554781; 9 pages.
Office Action dated Dec. 19, 2023, directed to CN Application No. 202080035260.6; 8 pages.
Office Action dated Jan. 11, 2023, directed to CO Application No. NC2021/0012391; 17 pages.
Office Action dated Nov. 28, 2023, directed to TW Application No. 109107889; 11 pages.

(Continued)

*Primary Examiner* — Jeffrey T. Palenik

(74) *Attorney, Agent, or Firm* — Morrison & Foerster LLP

(57) ABSTRACT

Softgels having improved stability of active pharmaceutical ingredients and methods of preparing the same are provided. In some embodiments, a softgel comprises a fill material composition and a softgel shell. In some embodiments, the fill material composition of the softgel comprises one or more active pharmaceutical ingredient (API); 2 to 15 wt. % povidone; 30 to 60 wt. % polyethylene glycol; and 0.5 to 5 wt. % propylene glycol, wherein the fill material composition has a pH of 3.75 or less. In some embodiments, the softgel shell is made from a softgel shell composition comprising an acidic component.

17 Claims, 13 Drawing Sheets

(56) References Cited

OTHER PUBLICATIONS

Office Action dated Aug. 1, 2023, directed to RU Application No. 2021129196; 15 pages.
Second Office Action dated Jul. 3, 2023, directed to CN Application No. 202080035260.6; 12 pages.
International Search Report and Written Opinion mailed Jun. 9, 2020, directed to International Application No. PCT/US2020/022114; 13 pages.
Communication pursuant to Article 94(3) EPC dated Aug. 26, 2024, directed to EP Application No. 20718423.5; 5 pages.
Examination Report No. 1 dated Dec. 10, 2024, directed to AU Application No. 2020235883; 3 pages.
Notice of Reexamination dated Dec. 25, 2024, directed to CN Application No. 202080035260.6; 21 pages.
Office Action dated Oct. 2, 2024, directed to MX Application No. MX/a/2021/010959; 9 pages.
Notice of Reasons for Rejection dated Oct. 7, 2024, directed to JP Application No. 2021-554781; 4 pages.
Office Action dated Apr. 26, 2023, directed to IN Application No. 202127045979; 5 pages.
Office Action dated Aug. 26, 2024, directed to EP Application No. 20718423.5; 5 pages.
Office Action dated Oct. 7, 2024, directed to JP Application No. 2021-554781; 4 pages.
Office Action dated Feb. 24, 2025, directed to MX Application No. MX/a/2021/010959; 7 pages.
Office Action dated Feb. 28, 2025, directed to CN Application No. 202080035260.6; 24 pages.
Office Action dated Jan. 7, 2025, directed to CO Application No. NC2021/0012391; 16 pages.
Office Action dated Mar. 10, 2025. directed to IL Application No. 286239; 5 pages.
Office Action date May 5, 2025, directed to TW Application No. 113124081; 10 pages.
Office Action dated Jun. 27, 2025, directed to KR Application No. 10-2021-7032620; 13 pages.
Office Action dated May 8, 2025, directed to MX Application No. MX/a/2021/010959; 11 pages.
Office Action dated Jul. 30, 2025, directed to CO Application No. NC2021/0012391; 12 pages.
Office Action dated Oct. 28, 2025, directed to JP Application No. 2024-158269; 11 pages.
Office Action dated Oct. 8, 2025, directed to AU Application No. 2020235883; 2 pages.
First Office Action dated Oct. 13, 2022, directed to CN Application No. 202080035260.6; 16 pages.

* cited by examiner

API STABILITY IN SOFTGELS

CROSS-REFERENCE TO RELATED APPLICATIONS

This application is a national stage application under 35 U.S.C. § 371 of International Application No. PCT/US2020/022114, filed on Mar. 11, 2020, which claims priority benefit to U.S. Provisional Patent Application No. 62/816,621, filed on Mar. 11, 2019, the disclosure of each of which is hereby incorporated herein by reference in its entirety.

FIELD OF THE INVENTION

This relates to softgels, and, particularly, to softgels having improved active pharmaceutical compound (API) stability with minimal instability over time.

BACKGROUND OF THE INVENTION

Softgels are a common dosage form for pharmaceutical compounds. Specifically, softgels are oral dosage forms for pharmaceuticals that are generally easier to swallow, resistant to tampering, and often cause less stomach discomfort than alternative dosage forms such as liquid, tablets, etc. Softgels comprise two primary components—a shell and a fill material. Some softgel shells can include gelatin, water, an opacifier, and a plasticizer. The fill material comprises the active pharmaceutical ingredient (API) and any of numerous inactive ingredients.

Sometimes undesirable reactions can occur between the softgel shell and the fill material of a softgel. For example, water from the softgel shell can migrate into the fill material, altering the physical and chemical properties of both the fill material and the softgel shell. Similarly, components of the fill material can migrate into the softgel shell, also altering the physical and chemical properties of both the fill material and the softgel shell. In addition to this, excipients and degradants of excipients can interact with the APIs in a negative manner. These reactions can detrimentally affect API efficacy, stability, etc. depending on the chemical components that migrate and participate in adverse reactions.

SUMMARY OF THE INVENTION

Described are fill material compositions, softgel shell compositions, softgel compositions, and methods for preparing the same. The provided compositions and methods of preparing said fill material compositions, softgel shell compositions, and softgel compositions have improved stability of one or more APIs by addressing problems with interactions between the softgel shell and the fill material of a softgel. These adverse reactions can occur between the softgel shell and the fill material of a softgel, detrimentally affecting the stability of one or more components of the softgel.

One or more APIs can degrade when exposed to specific inactive ingredients of a softgel. For example, phenylephrine can react with inactive ingredients of the fill material, such as povidone or PEG, causing the phenylephrine to break down. In some embodiments, degradants of inactive materials, such as povidone or PEG, can react with phenylephrine and cause it to break down. When APIs such as phenylephrine break down in a softgel, the stability of the phenylephrine is compromised. API instability can affect a softgel's shelf-life, strength, and/or effectiveness.

Accordingly, fill material compositions, softgel shell compositions, softgel compositions, and methods of making the same are directed to improving the stability of one or more APIs of the softgel. In some embodiments, a fill material composition may comprise an acidic solution. In some embodiments, a fill material composition may comprise an antioxidant. In some embodiments, a softgel shell composition may include an acidic solution. In some embodiments, controlling the pH of the fill material below the pKa of one or more degradant materials can improve the API stability of the softgel.

In some embodiments, a pharmaceutical softgel is provided, the softgel comprising a fill material composition comprising: one or more active pharmaceutical ingredient (API); 2 to 15 wt. % povidone; 30 to 60 wt. % polyethylene glycol; and 0.5 to 5 wt. % propylene glycol, wherein the fill material composition has a pH of 3.75 or less, and a softgel shell.

In some embodiments of the softgel, the softgel shell is made from a softgel shell composition comprising an acidic component.

In some embodiments of the softgel, the acidic component comprises hydrochloric acid.

In some embodiments of the softgel, the one or more API comprises ibuprofen, phenylephrine, dextromethorphan, acetaminophen, or guaifenesin.

In some embodiments of the softgel, the API comprises phenylephrine.

In some embodiments of the softgel, the fill material composition comprises 30 wt. % or greater total API.

In some embodiments of the softgel, softgel comprises 60 wt. % or less total API.

In some embodiments of the softgel, the povidone comprises one or more of povidone K-12 and povidone K-30.

In some embodiments of the softgel, the povidone comprises povidone K-30.

In some embodiments of the softgel, the polyethylene glycol comprises PEG 400.

In some embodiments of the softgel, the fill material composition comprises 0.5 wt. % to 1.0 wt. % of 0.5 N hydrochloric acid.

In some embodiments of the softgel, the softgel comprises from 1 wt. % to 2 wt. % of 25% potassium iodide.

In some embodiments, a fill material composition for a softgel is provided, the composition comprising: one or more active pharmaceutical ingredients (APIs), 2 to 15 wt. % povidone, 30 to 60 wt. % polyethylene glycol, and 0.5 to 5 wt. % propylene glycol, wherein the fill material composition has a pH of 3.75 or less.

In some embodiments of the composition, the one or more APIs comprise at least one of ibuprofen, phenylephrine, dextromethorphan, acetaminophen, and guaifenesin.

In some embodiments of the composition, the one or more APIs comprise phenylephrine.

In some embodiments of the composition, the composition comprises 30 wt. % or greater total API.

In some embodiments of the composition, the composition comprises 60 wt. % or less total API.

In some embodiments of the composition, the povidone comprises at least one of povidone K-12 and povidone K-30.

In some embodiments of the composition, the povidone comprises povidone K-30.

In some embodiments of the composition, the polyethylene glycol comprises PEG 400.

In some embodiments of the composition, the pH of 3.75 or less is achieved by mixing hydrochloric acid into the fill material composition.

In some embodiments of the composition, the composition comprises from 1 wt. % to 2 wt. % of 25% potassium iodide.

In some embodiments, a method of preparing a fill material composition for a softgel is provided, the method comprising: combining 30 to 60 wt. % polyethylene glycol, 0.5 to 5 wt. % propylene glycol, 2 to 15 wt. % povidone, one or more active pharmaceutical ingredient (API), and an acidic component to achieve a pH of 3.75 or less of the fill material composition.

In some embodiments of the method, the one or more API comprises ibuprofen, phenylephrine, dextromethorphan, acetaminophen, or guaifenesin.

In some embodiments of the method, the API comprises phenylephrine.

In some embodiments of the method, the method comprises 30 wt. % or greater API.

In some embodiments of the method, the method comprises 60 wt. % or less API.

In some embodiments of the method, the povidone comprises one or more of povidone K-12 and povidone K-30.

In some embodiments of the method, the povidone comprises povidone K-30.

In some embodiments of the method, the polyethylene glycol comprises PEG 400.

In some embodiments of the method, the acidic component comprises 0.5 wt. % to 1.0 wt. % of 0.5 N hydrochloric acid.

In some embodiments of the method, the method comprises 1 wt. % to 2 wt. % of 25% potassium iodide.

In some embodiments, a method of preparing a softgel is provided, the method comprising: combining 30 to 60 wt. % polyethylene glycol, 0.5 to 5 wt. % propylene glycol, 2 to 15 wt. % povidone, one or more active pharmaceutical ingredient (API), and an acidic component to form a fill material comprising a pH of 3.75 or less; and encapsulating the fill material in a softgel shell to form a softgel.

In some embodiments of the method, the softgel shell is made from a softgel shell composition comprising an acidic component.

In some embodiments of the method, the acidic component comprises hydrochloric acid.

In some embodiments of the method, the one or more API comprises ibuprofen, phenylephrine, dextromethorphan, acetaminophen, or guaifenesin.

In some embodiments of the method, the API comprises phenylephrine.

In some embodiments of the method, the method comprises 30 wt. % or greater API.

In some embodiments of the method, the method comprises 60 wt. % or less API.

In some embodiments of the method, the povidone comprises one or more of povidone K-12 and povidone K-30.

In some embodiments of the method, the povidone comprises povidone K-30.

In some embodiments of the method, the polyethylene glycol comprises PEG 400.

In some embodiments of the method, the method comprises adding an acid comprises 0.5 wt. % to 1.0 wt. % of 0.5 N hydrochloric acid.

4 In some embodiments of the method, preparing a fill material composition comprises adding 1 wt. % to 2 wt. % of 25% potassium iodide.

BRIEF DESCRIPTION OF THE DRAWINGS

The invention will now be described, by way of example only, with reference to the accompanying drawings, in which.

DETAILED DESCRIPTION OF THE INVENTION

Figure 1:
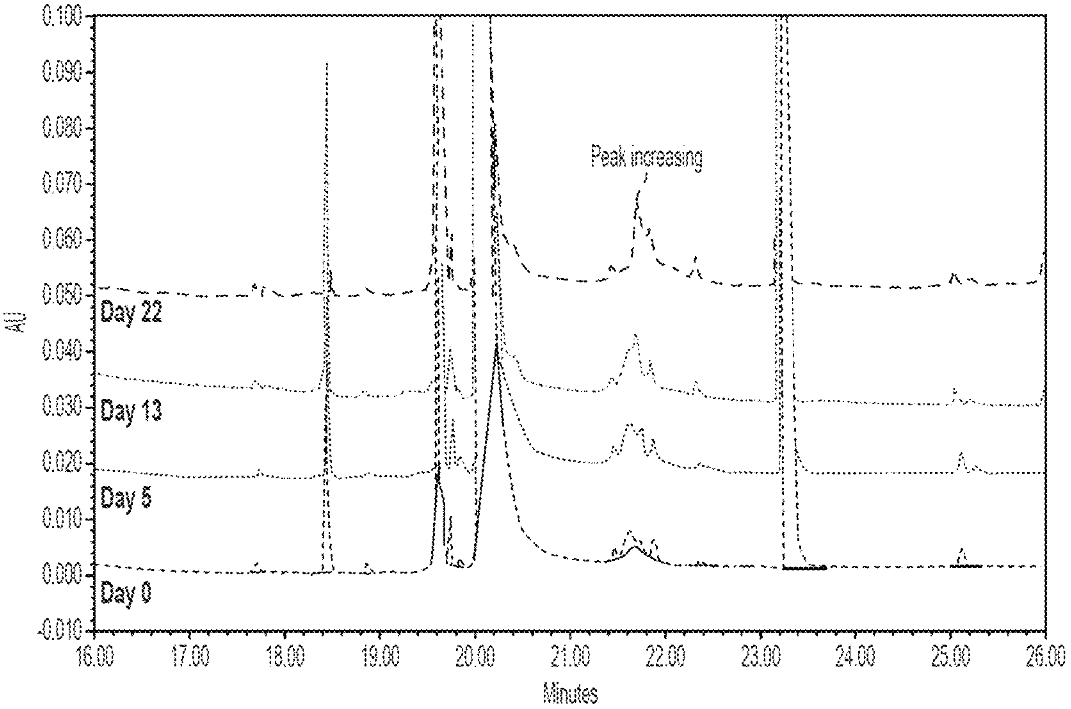
FIG. 1 shows chromatogram overlays of PE assays stressed at 70° C., revealing a peak at approximately 21.6 minutes according to some embodiments.

Described are exemplary embodiments of fill material compositions, softgel shell compositions, and softgel compositions having improved API stability, as well as methods for making fill materials, softgel shells, and softgels having improved API stability. As described above, fill materials can interact with each other and with softgel shells of a formed softgel and cause instability of one or more components of the softgel shell and/or fill material. Embodiments described herein are directed to stabilizing one or more APIs of the fill material in a prepared softgel.

In some embodiments, phenylephrine may interact with inactive ingredients of the fill material directly or possibly interact with the degradants of the inactive ingredients. This interaction can cause phenylephrine to break down in the softgel, causing a shorter shelf-life, a lower strength, and/or a lower effectiveness of the softgel. In some embodiments, other APIs such as ibuprofen, guaifenesin, dextromethorphan, acetaminophen, and/or benzonatate may experience instability due to interactions with inactive ingredients of the fill material. In some embodiments, one or more APIs (e.g., phenylephrine) may break down by interacting with inactive ingredients such as povidone or PEG. In some embodiments, one or more APIs (e.g., phenylephrine) may break down by interacting with a degradant of one or more inactive ingredients, such as povidone or PEG.

Accordingly, some embodiments provided herein are directed to improving API (e.g., phenylephrine) stability in softgels by controlling the pH of the fill material. In particular, it has been determined that controlling the pH of the fill material below the pKa of the degradants of povidone and/or PEG can inhibit phenylephrine from reacting with the povidone and PEG degradants. For example, the fill material may be controlled to a pH of 3.75 or less. By inhibiting reactions between phenylephrine and degradants of povidone and/or PEG, the stability of phenylephrine is improved. Improved phenylephrine stability can improve shelf-life, strength, and/or effectiveness of the softgel.

In some embodiments, the pH of the fill material is controlled by adding an acidic solution to the fill material. In some embodiments, the pH of the fill material is controlled by adding an acidic solution to the softgel shell. In some embodiments, degradation of inactive ingredients (e.g., povidone, PEG) is minimized by adding an antioxidant to the fill material. Controlling the degradation of inactive ingredients such as povidone and PEG can improve API stability by limiting the amount of degradants the API (e.g., phenylephrine) can react with.

Following is a discussion of (1) the instability of APIs in softgels generally; (2) fill material compositions comprising the API phenylephrine (PE) specifically; (3) softgel shell compositions; and (4) methods of preparing fill material compositions and softgels. These are each discussed in turn below.

Instability of Active Pharmaceutical Ingredients (APIs) in Softgels

Provided below is a description of the instability of APIs in softgels. API stability is a common problem in softgel compositions more so than in other pharmaceutical forms (e.g., tablets, liquid, etc.). Examples of APIs and causes for API instability in softgels are discussed.

Various APIs are suitable for use in softgels. For example, common APIs that are prepared in softgel form alone or in combination include ibuprofen, phenylephrine, guaifenesin, dextromethorphan, acetaminophen, naproxen, diphenhydramine, docusate sodium, loratadine, cetirizine, pseudoephedrine, doxylamine, chlorpheniramine, diclofenac, and benzonatate. A skilled artisan can readily identify other suitable APIs for use in the disclosed embodiments.

One example of an API that may be used in a softgel is phenylephrine (PE). PE is a vasoconstrictor and decongestant. Most commonly, PE can be used to treat common cold symptoms (i.e., stuffy nose), sinus issues, and hemorrhoids. The instability of various APIs in softgels, and in particular the instability of PE, is a well-known problem.

The instability of PE is believed to be due to the degradation of one or more inactive ingredients (i.e., excipients) in the fill material and/or softgel shell of the softgel. Inactive ingredients that can degrade and adversely react with an API such as PE include polyethylene glycol (PEG) and povidone (also "polyvinylpyrrolidone" or "PVP"). For example, PEG is a common excipient used in the fill material of a softgel. When PEG degrades, the PEG degradants interact with the PE, causing the PE to degrade. For example, PEG may break down into aldehydes and/or short chain organic acids, both of which readily react with PE.

PEG is known to readily degrade into several short chain organic acids and aldehydes (impurities) when in the presence of oxygen and/or water. Short chain organic acids can include formic acid, acetic acid, and/or glycolic acid. Aldehydes can include formaldehyde and/or acetaldehyde. These PEG degradants are known to readily interact with PE, causing the degradation of PE in the fill material of a softgel.

Similarly, povidone can also degrade into compounds including peroxides and short chain acids such as formic acid. Like the degradants of PEG, the degradants of povidone can also adversely react with APIs such as PE. In particular, certain varieties of povidone may be more susceptible to interacting with PE than others. For example, povidone K-30 more readily reacts with PE than povidone K-12. This is believed to be in part due to the different terminal groups between povidone K-12 and povidone K-30. In particular, povidone K-12 uses isopropanol during synthesis resulting in propyl terminal groups, whereas povidone K-30 uses water during synthesis, resulting in hydroxyl terminal groups. PE readily reacts with hydroxyl groups, such as the hydroxyl terminal groups of povidone K-30. Thus, PE more readily interacts with povidone K-30 than povidone K-12. Below is provided the chemical structures of povidone K-12, povidone K-30, and PE.

Povidone K-12 (povidone synthesized with isopropanol):

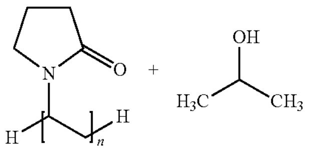

Povidone K-30 (povidone synthesized with water):

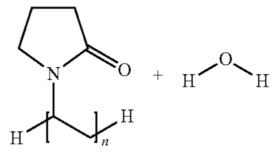

Phenylephrine (PE):

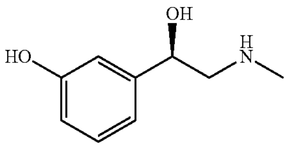

When PE reacts with degradants of PEG and/or povidone, it breaks down within the softgel. This breakdown is indicative of PE instability. PE instability can lead to a shorter shelf-life, a lower strength, an increase in possibly harmful impurities, and/or a lower effectiveness of the softgel.

Accordingly, to reduce the instability of PE in softgels, a method to reduce the interactions between PE and PEG and/or povidone may be employed. Conventional methods of reducing the instability of PE include using antioxidants to reduce the amount of PEG and/or povidone degradation.

However, methods for improving the stability of PE according to embodiments disclosed herein include preventing the interaction between PE and the PEG/povidone degradants and not necessarily inhibiting PEG and/or povidone degradation. Some embodiments may include methods of minimizing interactions between PE and PEG/povidone degradants as well as minimizing the degradation of PEG/povidone.

Described below are various embodiments directed to limiting various interactions between one or more APIs (e.g., PE) and degradants such as those formed from the degradation of PEG and/or povidone. In some embodiments, introducing an acidic solution to the fill material and/or the softgel shell can improve API stability. Some embodiments may include an antioxidant such as potassium iodide (KI) in the fill material to improve API stability. In some embodiments, maintaining the pH of the fill material below the pKa of the PEG and/or povidone degradants can inhibit interactions between the PEG and/or povidone degradants and the PE.

Fill Material Compositions with Improved Phenylephrine (PE) Stability

Following is a description of fill material compositions developed for improved API stability. Fill material compositions provided herein may be encapsulated with a softgel shell to form an administrable pharmaceutical composition. In some embodiments, the fill material composition may include an acidic solution for improved API stability (e.g., improved PE stability). In some embodiments, the fill material composition may include an antioxidant to inhibit the degradation of one or more inactive ingredients for improved API stability.

In some embodiments, APAP may experience forms of instability in a fill material composition. For example, APAP may precipitate out of solution. However, it has been determined that the type and amount of povidone (i.e., povidone K-12 and/or povidone K-30) and/or the amount of propylene glycol in a fill material composition can affect APAP precipitation. Accordingly, some embodiments of fill material compositions provided herein may include an optimized amount of a specific type of povidone and/or propylene glycol to control the stability of APAP. Suggested amounts of povidone and propylene glycol to include in a fill material composition are provided below.

Example 1A below describes the effects of povidone and/or PEG on the stability of APAP in more detail. For example, the amount of APAP precipitation may correlate with the level of povidone K-30 and/or propylene glycol in a fill material composition. In some embodiments, increasing the levels of both povidone K-30 and propylene glycol can minimize APAP precipitation. In some embodiments, decreasing the level of plasticizers in the softgel shell can also minimize APAP precipitation.

In some embodiments, the type and/or amount of excipient may affect the stability of other APIs in solution as well. For example, APIs such as ibuprofen, phenylephrine, guaifenesin, dextromethorphan, and benzonatate may also exhibit similar behaviors as APAP, described above. In some embodiments, variations of other inactive ingredients such as PEG (i.e., PEG400, PEG600, PEG1200, PEG2400) may similarly impact the stability of one or more APIs in solution.

For example, as described above, povidone K-30 has a tendency to interact with PE. The interaction between povidone K-30 (including any povidone K-30 degradants) and PE can cause PE instability (i.e., when the amount of PE in the fill material composition decreases over time).

However, it has been determined that controlling the pH of the fill material composition can minimize interactions between povidone K-30 (and/or povidone K-30 degradants) and PE, and thus improve PE stability of the fill material composition. In some embodiments, a fill material composition may include an acidic solution to control the pH of the fill material composition. In some embodiments, the acidic solution may comprise citric acid, formic acid, acetic acid, and/or hydrochloric acid (HCl). Several tests were conducted in which HCl was introduced in the fill material composition, described in the Examples section below. The acidic solution should not be limited to materials comprising HCl. One of ordinary skill in the art will recognize that any suitable acidic solution may be used to control the pH of the fill material composition.

In some embodiments, an antioxidant may be included in the fill material composition as well. For example, an antioxidant may help control the formation of species corresponding to PE instability. Thus, even though KI has little effect on the interaction between PE and povidone/PEG degradants, it may still help to control the formation of other PE-related, APAP-related, and/or dextromethorphan-related substances when present in the fill material composition. For example, the presence of KI in the fill material composition material may also have a beneficial effect on controlling the formation of PE RS-3, one example of a PE-related degradant. PE RS-3 increases under acidic conditions. Thus, levels of PE RS-3 may increase if an acidic solution is added to the fill material composition. Adding an antioxidant such as KI may help control the levels of PE RS-3. Also, the addition of KI can help reduce the formation of 4-aminophenol from APAP as well as stop the formation of N-oxide degradants of dextromethorphan and doxylamine. Examples of antioxidants include potassium iodide, propyl gallate, butylated hydroxytoluene, butylated hydroxyanisole, and other suitable antioxidants.

Accordingly, some embodiments provided herein may include an acid to minimize the interaction between PE and degradants of one or more inactive ingredients. Some embodiments may also include an antioxidant, such as KI, to reduce the degradation of one or more inactive ingredients and thus, to reduce the presence of certain degradants that may otherwise contribute to the instability of the API.

Below is provided various components and amounts of components that may comprise a fill material composition to form a softgel according to embodiments provided herein.

As used herein, “active pharmaceutical ingredient” or “API” refers to a drug product that may be used in the diagnosis, cure, mitigation, treatment, or prevention of disease. Any API may be used for purposes of the present disclosure. Suitable APIs include, without limitation: analgesics and anti-inflammatory agents, antacids, anthelmintics, anti-arrhythmic agents, anti-bacterial agents, anti-coagulants, anti-depressants, anti-diabetics, anti-diarrheals, anti-epileptics, anti-fungal agents, anti-gout agents, antihypertensive agents, anti-malarials, anti-migraine agents, anti-muscarinic agents, anti-neoplastic agents and immunosuppressants, anti-protazoal agents, antirheumatics, anti-thyroid agents, antivirals, anxiolytics, sedatives, hypnotics and neuroleptics, beta-blockers, cardiac inotropic agents, corticosteroids, cough suppressants, cytotoxics, decongestants, diuretics, enzymes, anti-parkinsonian agents, gastro-intestinal agents, histamine receptor antagonists, lipid regulating agents, local anesthetics, neuromuscular agents, nitrates and anti-anginal agents, nutritional agents, opioid analgesics, oral vaccines, proteins, peptides and recombinant drugs, sex hormones and contraceptives, spermicides, and stimulants;

and combinations thereof. When present, the API is present in the pharmaceutical composition in an amount that is necessary to exhibit the required physiological effect as established by clinical studies. One of ordinary skill in the art can readily determine an appropriate amount of API to include in the dosage form made according to the present disclosure.

In some embodiments, the fill material composition may include from 15 to 70 wt. % total API, from 20 to 65 wt. % total API, from 25 to 60 wt. % total API, from 30 to 55 wt. % total API, from 35 to 55 wt. % total API, or from 40 to 50 wt. % total API. In some embodiments, the fill material composition may include less than 70 wt. % total API, less than 65 wt. % total API, less than 60 wt. % total API, less than 55 wt. % total API, less than 50 wt. % total API, less than 45 wt. % total API, less than 40 wt. % total API, less than 35 wt. % total API, less than 30 wt. % total API, less than 25 wt. % total API, or less than 20 wt. % total API. In some embodiments, the fill material composition may include more than 15 wt. % total API, more than 20 wt. % total API, more than 25 wt. % total API, more than 30 wt. % total API, more than 35 wt. % total API, more than 40 wt. % total API, more than 45 wt. % total API, more than 50 wt. % total API, more than 55 wt. % total API, more than 60 wt. % total API, or more than 65 wt. % total API.

In some embodiments, the fill material composition may comprise PE. For example, the fill material composition may include from 0.1 to 15 wt. % PE, from 0.2 to 10 wt. % PE, from 0.3 to 5 wt. % PE, or from 0.3 to 1 wt. % PE. In some embodiments, the fill material composition may include less than 15 wt. % PE, less than 12 wt. % PE, less than 10 wt. % PE, less than 8 wt. % PE, less than 5 wt. % PE, 4 wt. % PE, less than 3 wt. % PE, less than 2 wt. % PE, less than 1.0 wt. % PE, less than 0.9 wt. % PE, less than 0.8 wt. % PE, less than 0.7 wt. % PE, less than 0.6 wt. % PE, less than 0.5 wt. % PE, less than 0.4 wt. % PE, less than 0.3 wt. % PE, or less than 0.2 wt. % PE. In some embodiments, the fill material composition may include more than 0.1 wt. % PE, more than 0.2 wt. % PE, more than 0.3 wt. PE, more than 0.4 wt. % PE, more than 0.5 wt. % PE, more than 0.6 wt. % PE, more than 0.7 wt. % PE, more than 0.8 wt. % PE, more than 0.9 wt. % PE, more than 1.0 wt. % PE, more than 2 wt. % PE, more than 3 wt. % PE, more than 4 wt. % PE, more than 5 wt. % PE, more than 8 wt. % PE, more than 10 wt. % PE, or more than 12 wt. % PE.

In some embodiments, the fill material composition may include APAP. For example, the fill material composition may comprise from 10 to 50 wt. % APAP, from 15 to 45 wt. % APAP, from 20 to 40 wt. % APAP, or from 25 to 35 wt. % APAP. In some embodiments, the fill material composition may include less than 50 wt. % APAP, less than 45 wt. % APAP, less than 40 wt. % APAP, less than 35 wt. % APAP, less than 30 wt. % APAP, less than 25 wt. % APAP, less than 20 wt. % APAP, or less than 15 wt. % APAP. In some embodiments, the fill material composition may include more than 10 wt. % APAP, more than 15 wt. % APAP, more than 20 wt. % APAP, more than 25 wt. % APAP, more than 30 wt. % APAP, more than 35 wt. % APAP, more than 40 wt. % APAP, or more than 45 wt. % APAP.

In some embodiments, the fill material composition may include dextromethorphan. For example, the fill material composition may comprise from 0.2 to 12 wt. % dextromethorphan, from 0.4 to 10 wt. %, from 0.6 to 5 wt. %, or from 0.7 to 1.0 wt. % dextromethorphan. In some embodiments, the fill material composition may include less than 12 wt. %, less than 10 wt. %, less than 8 wt. %, less than 5 wt. %, less than 4 wt. %, less than 3 wt. %, less than 2 wt. %, less than 1.8 wt. %, less than 1.6 wt. %, less than 1.4 wt. %, less than 1.2 wt. %, less than 1.0 wt. %, less than 0.8 wt. %, less than 0.6 wt. %, or less than 0.4 wt. % dextromethorphan. In some embodiments, the fill material composition may include more than 0.2 wt. %, more than 0.4 wt. %, more than 0.6 wt. %, more than 0.8 wt. %, more than 1.0 wt. %, more than 1.2 wt. %, more than 1.4 wt. %, more than 1.6 wt. %, more than 1.8 wt. %, more than 2 wt. %, more than 3 wt. %, more than 4 wt. %, more than 5 wt. %, more than 8 wt. %, or more than 10 wt. % dextromethorphan.

In some embodiments, the fill material composition may include guaifenesin. For example, the fill material composition may comprise from 5 to 30 wt. % guaifenesin, from 10 to 25 wt. %, or from 15 to 20 wt. % guaifenesin. In some embodiments, the fill material composition may include less than 30 wt. %, less than 25 wt. %, less than 20 wt. %, less than 15 wt. %, or less than 10 wt. % guaifenesin. In some embodiments, the fill material composition may include more than 5 wt. %, more than 10 wt. %, more than 15 wt. %, more than 20 wt. %, or more than 25 wt. % guaifenesin.

The fill material composition may include any of numerous types of inactive ingredients (i.e., excipients). In some embodiments, the fill material composition may include from 30 to 80 wt. % total inactive ingredients, from 35 to 75 wt. %, from 40 to 70 wt. %, from 45 to 65 wt. %, or from 50 to 60 wt. % total inactive ingredients. In some embodiments, the fill material composition may include less than 80 wt. %, less than 75 wt. %, less than 70 wt. %, less than 65 wt. %, less than 60 wt. %, less than 55 wt. %, less than 50 wt. %, less than 45 wt. %, or less than 40 wt. % total inactive ingredients. In some embodiments, the fill material composition may include more than 30 wt. %, more than 35 wt. %, more than 40 wt. %, more than 45 wt. %, more than 50 wt. %, more than 55 wt. %, more than 60 wt. %, more than 65 wt. %, or more than 70 wt. % total inactive ingredients.

Some embodiments of the fill material composition may include specific inactive ingredients such as polyethylene glycol (PEG), propylene glycol, povidone, and/or purified water. PEG may include any of PEG400, PEG600, PEG1200, and/or PEG2400. In some embodiments, the fill material composition may include from 30 to 60 wt. % PEG, from 35 to 55 wt. %, or from 40 to 50 wt. % PEG. In some embodiments, the fill material composition may include less than 60 wt. %, less than 55 wt. %, less than 50 wt. %, less than 45 wt. %, less than 40 wt. %, or less than 35 wt. % PEG. In some embodiments, the fill material composition may include more than 30 wt. %, more than 35 wt. %, more than 40 wt. %, more than 45 wt. %, more than 50 wt. %, or more than 55 wt. % PEG.

In some embodiments, the fill material composition may include povidone. For example, some embodiments may include povidone K-12 and/or povidone K-30. In some embodiments, the fill material composition may include from 2 to 30 wt. % povidone, from 3 to 25 wt. %, from 4 to 20 wt. %, or from 5 to 15 wt. % povidone. In some embodiments, the fill material composition may include less than 30 wt. %, less than 25 wt. %, less than 20 wt. %, less than 15 wt. %, less than 12 wt. %, less than 10 wt. %, less than 8 wt. %, less than 5 wt. %, or less than 4 wt. % povidone. In some embodiments, the fill material composition may include more than 2 wt. %, more than 3 wt. %, more than 4 wt. %, more than 5 wt. %, more than 8 wt. %, more than 10 wt. %, more than 12 wt. %, more than 15 wt. %, more than 20 wt. %, or more than 25 wt. % povidone.

In some embodiments, the fill material composition may include propylene glycol. In some embodiments, the fill material composition may include from 0.25 to 10.0 wt. %, from 0.5 to 5.0 wt. %, or from 0.75 to 3.0 wt. % propylene glycol. In some embodiments, the fill material composition may include more than 0.25 wt. %, more than 0.5 wt. %, more than 0.75 wt. %, more than 1.0 wt. %, more than 1.25 wt. %, more than 1.5 wt. %, more than 1.75 wt. %, more than 2.0 wt. %, more than 2.5 wt. %, more than 3.0 wt. %, more than 3.5 wt. %, more than 4.0 wt. %, more than 4.5 wt. %, more than 5.0 wt. %, more than 5.5 wt. %, more than 6.0 wt. %, more than 6.5 wt. %, more than 7.0 wt. %, more than 8.0 wt. %, or more than 9.0 wt. % propylene glycol. In some embodiments, the fill composition may include less than 10.0 wt. %, less than 9.0 wt. %, less than 8.0 wt. %, less than 7.0 wt. %, less than 6.5 wt. %, less than 6.0 wt. %, less than 5.5 wt. %, less than 5.0 wt. %, less than 4.5 wt. %, less than 4.0 wt. %, less than 3.5 wt. %, less than 3.0 wt. %, less than 2.5 wt. %, less than 2.0 wt. %, less than 1.75 wt. %, less than 1.5 wt. %, less than 1.25 wt. %, less than 1.0 wt. %, less than 0.75 wt. %, or less than 0.50 wt. % propylene glycol.

In some embodiments, the fill material composition may include an acidic solution. For example, the acidic solution may include one or more of citric acid, formic acid, acetic acid, hydrochloric acid (HCl), or any other suitable acidic material. In some embodiments, the acidic solution may have a concentration from 0.05 to 0.5 N, from 0.075 to 0.3 N, or from 0.10 to 0.20 N. In some embodiments, the concentration may be less than 0.5 N, less than 0.4 N, less than 0.3 N, less than 0.25 N, less than 0.20 N, less than 0.15 N, less than 0.10 N, less than 0.08 N, or less than 0.075 N. In some embodiments, the acidic solution may have a concentration of more than 0.05 N, more than 0.075 N, more than 0.08 N, more than 0.10 N, more than 0.125 N, more than 0.15 N, more than 0.175 N, more than 0.20 N, more than 0.25 N, more than 0.30 N, or more than 0.40 N. In some embodiments, the fill material composition may include from 0.25-10.0 wt. %, from 0.5-8.0 wt. %, or from 1.0-5.0 wt. % acidic solution. In some embodiments, the fill material composition may include more than 0.25 wt. %, more than 0.50 wt. %, more than 0.75 wt. %, more than 1.0 wt. %, more than 1.5 wt. %, more than 2.0 wt. %, more than 2.5 wt. %, more than 3.0 wt. %, more than 3.5 wt. %, more than 4.0 wt. %, more than 4.5 wt. %, more than 5.0 wt. %, more than 6.0 wt. %, more than 7.0 wt. %, more than 8.0 wt. %, or more than 9.0 wt. % acidic solution. In some embodiments, the fill material composition may include less than 10.0 wt. %, less than 9.0 wt. %, less than 8.0 wt. %, less than 7.0 wt. %, less than 6.0 wt. %, less than 5.5 wt. %, less than 5.0 wt. %, less than 4.5 wt. %, less than 4.0 wt. %, less than 3.5 wt. %, less than 3.0 wt. %, less than 2.5 wt. %, less than 2.0 wt. %, less than 1.75 wt. %, less than 1.50 wt. %, less than 1.25 wt. %, less than 1.0 wt. %, less than 0.75 wt. %, or less than 0.50 wt. % acidic solution.

In some embodiments, the fill material composition may include an antioxidant. Examples of antioxidants may include potassium iodide, propyl gallate, butylated hydroxytoluene, butylated hydroxyanisole, and other suitable antioxidants. In some embodiments, a fill material composition may include from 0.25 to 5.0 wt. %, 0.5 to 4.0 wt. %, or 1.0 to 2.0 wt. % antioxidants. In some embodiments, the fill material composition may include more than 0.25 wt. %, more than 0.5 wt. %, more than 0.75 wt. %, more than 1.0 wt. %, more than 1.25 wt. %, more than 1.50 wt. %, more than 1.75 wt. %, more than 2.0 wt. %, more than 2.5 wt. %, more than 3.0 wt. %, more than 3.5 wt. %, more than 4.0 wt. %, or more than 4.5 wt. % antioxidants. In some embodiments, the fill material composition may include less than 5.0 wt. %, less than 4.5 wt. %, less than 4.0 wt. %, less than 3.5 wt. %, less than 3.0 wt. %, less than 2.5 wt. %, less than 2.0 wt. %, less than 1.75 wt. %, less than 1.5 wt. %, less than 1.25 wt. %, less than 1.0 wt. %, less than 0.75 wt. %, or less than 0.50 wt. % antioxidants.

In some embodiments, the fill material composition may include one or more solvents. For example, the solvent may be water (e.g., purified water). In some embodiments, the fill material composition may include from 1 to 10 wt. % solvent, from 1.5 to 9 wt. %, from 2 to 8 wt. %, from 2.5 to 7 wt. %, from 3 to 6 wt. %, or from 3.5 to 5 wt. % solvent. In some embodiments, the fill material composition may include less than 10 wt. %, less than 9 wt. %, less than 8 wt. %, less than 7 wt. %, less than 6 wt. %, less than 5 wt. %, less than 4 wt. %, less than 3 wt. %, or less than 2 wt. % solvent. In some embodiments, the fill material composition may include more than 1 wt. %, more than 2 wt. %, more than 3 wt. %, more than 4 wt. %, more than 5 wt. %, more than 6 wt. %, more than 7 wt. %, more than 8 wt. %, or more than 9 wt. % solvent.

Softgel Shell Compositions

Provided below is a description of softgel shells formulated for improved API stability of a softgel. Softgel shells are often gelatin-based shells surrounding a fill material composition (described in detail above). Softgel shells typically include gelatin, opacifiers, plasticizers, and water. In some embodiments, a softgel shell may include an acidic solution for improved API stability of a softgel.

In some embodiments, once a fill material (i.e., a fill material according to any of the composition embodiments described above) is encapsulated by a softgel shell, one or more APIs of the fill material may experience instability over time. In particular, migration of components from the softgel shell to the fill material can alter the pH of the fill material, causing instability of one or more APIs (e.g., PE). Accordingly, it has been discovered that including an acidic solution in the softgel shell of a softgel may help maintain API stability of the fill material in the softgel. With an acidic softgel shell, the acidic solution of the fill material will be less likely to migrate to the shell of a softgel. Thus, the acidic environment of the fill material may be maintained upon encapsulation by a softgel shell to minimize reactions between an API and degradant(s) of one or more inactive ingredients. Provided below are components and amounts for components of a softgel shell according to some embodiments provided herein.

Although most softgel shells are gelatin-based, some embodiments of softgel shells may comprise other materials such as carrageenan, starch, or another suitable gelling agent. In some embodiments, the softgel shell may comprise from 15 wt. % to 70 wt. %, from 30 wt. % to 50 wt. %, or from 40 wt. % to 45 wt. % gelling agent. In some embodiments, the softgel shell may comprise less than 70 wt. %, less than 65 wt. %, less than 60 wt. %, less than 55 wt. %, less than 50 wt. %, less than 45 wt. %, less than 40 wt. %, less than 35 wt. %, less than 30 wt. %, less than 25 wt. %, or less than 20 wt. % gelling agent. In some embodiments, the softgel shell may comprise more than 15 wt. %, more than 20 wt. %, more than 25 wt. %, more than 30 wt. %, more than 35 wt. %, more than 40 wt. %, more than 45 wt. %, more than 50 wt. %, more than 55 wt. %, more than 60 wt. %, or more than 65 wt. % gelling agent.

As described above, a softgel shell may include an opacifier to make the shell opaque in appearance. Examples of opacifiers include titanium dioxide, zinc oxide, and calcium carbonate. In some embodiments, a softgel shell may include from 0.1 to 5 wt. %, from 0.3 to 3 wt. %, or from 0.5 to 1.0 wt. % opacifier. In some embodiments, a softgel shell may include less than 5 wt. %, less than 4.5 wt.

%, less than 4.0 wt. %, less than 3.5 wt. %, less than 3.0 wt. %, less than 2.5 wt. %, less than 2.0 wt. %, less than 1.5 wt. %, less than 1.0 wt. %, less than 0.9 wt. %, less than 0.8 wt. %, less than 0.7 wt. %, less than 0.6 wt. %, less than 0.5 wt. %, less than 0.4 wt. %, less than 0.3 wt. %, or less than 0.2 wt. % opacifier. In some embodiments, a softgel shell may include more than 0.1 wt. %, more than 0.2 wt. %, more than 0.3 wt. %, more than 0.4 wt. %, more than 0.5 wt. %, more than 0.6 wt. %, more than 0.7 wt. %, more than 0.8 wt. %, more than 0.9 wt. %, more than 1.0 wt. %, more than 1.5 wt. %, more than 2.0 wt. %, more than 2.5 wt. %, more than 3.0 wt. %, more than 3.5 wt. %, more than 4.0 wt. %, or more than 4.5 wt. % opacifier.

Example plasticizers in a softgel shell may include sorbitol, glycerin, and/or other suitable plasticizers for pharmaceutical use. In some embodiments, the softgel shell may comprise from 10 to 40 wt. %, or from 20 to 30 wt. % plasticizer. In some embodiments, a softgel shell may include less than 40 wt. %, less than 35 wt. %, less than 30 wt. %, less than 25 wt. %, less than 20 wt. %, or less than 15 wt. % plasticizer. In some embodiments, a softgel shell may include more than 10 wt. %, more than 15 wt. %, more than 20 wt. %, more than 25 wt. %, more than 30 wt. %, or more than 35 wt. % plasticizer.

In some embodiments, as described above, the softgel shell may comprise an acidic solution. For example, the acidic solution may be one or more of citric acid, formic acid, acetic acid, and/or hydrochloric acid (HCl). In some embodiments, a softgel shell may comprise from 1 wt. % to 20 wt. %, from 2 wt. % to 15 wt. %, or from 3 wt. % to 8 wt. % acidic solution. In some embodiments, a softgel shell may comprise less than 20 wt. %, less than 18 wt. %, less than 15 wt. %, less than 12 wt. %, less than 10 wt. %, less than 8 wt. %, less than 5 wt. %, less than 4 wt. %, less than 3 wt. %, or less than 2 wt. % acidic solution. In some embodiments, a softgel shell may comprise more than 1 wt. %, more than 2 wt. %, more than 3 wt. %, more than 4 wt. %, more than 5 wt. %, more than 8 wt. %, more than 10 wt. %, more than 12 wt. %, more than 15 wt. %, or more than 18 wt. % acidic solution.

In some embodiments, the softgel shell may comprise water. For example, a softgel shell may comprise 30 to 60 wt. %, 35 to 55 wt. %, or 40 to 50 wt. % water. In some embodiments, a softgel shell may comprise more than 30 wt. %, more than 35 wt. %, more than 40 wt. %, more than 45 wt. %, more than 50 wt. %, or more than 55 wt. % water. In some embodiments, a softgel shell may comprise less than 60 wt. %, less than 55 wt. %, less than 50 wt. %, less than 45 wt. %, less than 40 wt. %, or less than 35 wt. % water.

Softgel shells may also include additional materials such as coloring agents, flavors, sugars, aromatic and other sensory agents, etc. A skilled artisan can readily determine suitable types of coloring agents appropriate for embodiments of the present invention.

Methods of Preparing Fill Material Compositions and Softgels

Provided below is a description of methods for preparing fill material compositions and softgels having improved API stability. Generally, fill material compositions and softgels described herein can be prepared using techniques that should be readily discernible by a person having ordinary skill in the art.

For example, fill material compositions may be prepared by mixing the necessary components, described in detail above, into an appropriate mixing vessel. An appropriate mixing vessel may be an OLSA 200 L mixing vessel, OLSA 2000 L mixing vessel, or any other suitable closed system with high shear mixing, temperature control, and nitrogen-blanketing capabilities. Some APIs, such as APAP, may need to be dissolved in the solution. After all components have been mixed appropriately, the solution can be de-aerated and cooled.

To encapsulate the fill material composition with a softgel shell, an encapsulation machine may be used. For example, a 6-inch or 7.24-inch encapsulation machine or any other suitable encapsulation device may be used to encapsulate the fill material composition. After encapsulation, the softgels can be dried until a pre-defined hardness is achieved.

EXAMPLES

Further details, including specific test data, for some embodiments generally described above are provided below.

Example 1: Fill material compositions were prepared and tested to observe physical and chemical stability characteristics. Specifically, fill material compositions were prepared comprising the APIs acetaminophen, guaifenesin, dextromethorphan, and phenylephrine, and inactive ingredients including PEG, propylene glycol, povidone, and water. The physical and chemical stability of the fill material composition were tested, as described below.

Example 1A—Physical Stability: To evaluate the physical stability of fill material compositions, fill material compositions according to embodiments described were encapsulated in a conventional softgel shell (i.e., a softgel shell not specifically formulated to maintain an acidic pH in the fill material composition according to embodiments described above) and observed under ambient conditions. The components of the specific fill material compositions tested are provided in Table 1. In the initial trials, APAP readily precipitated out of solution.

The type and amount of povidone was varied to test its impact on APAP precipitation. Fill material composition A (according to Table 1, below) included an increased amount of povidone K-30. The amounts of PEG400, propylene glycol, and water were adjusted to account for the increased povidone, but remained relatively similar to the amounts in the original fill material composition. Fill material composition B included povidone K-12 instead of povidone K-30. The specific amounts of the components of both fill material composition A and fill material composition B are provided in Table 1, below.

TABLE 1

Two example fill material compositions.

| Component | Composition A (wt. %) | Composition B (wt. %) |
|---|---|---|
| PEG 400 | 42.8 | 42.8 |
| Propylene glycol | 1.5 | 1.5 |
| Povidone K-12 | 6.7 | 0 |
| Povidone K-30 | 0 | 6.7 |
| Acetaminophen | 27.1 | 27.1 |
| Phenylephrine | 0.4 | 0.4 |
| Dextromethorphan | 0.8 | 0.8 |
| Guaifenesin | 16.7 | 16.7 |
| Purified water | 4.0 | 4.0 |

Both fill material compositions of Table 1 (i.e., fill material composition A and fill material composition B) were prepared and encapsulated in a conventional softgel shell and observed over time. For fill material composition A comprising povidone K-12, APAP was observed precipitating out of solution as early as one week after composition and encapsulation. However, for fill material composition B comprising povidone K-30, APAP did not precipitate out of solution until closer to two weeks after composition and encapsulation. Similarly, other fill material compositions were tested to evaluate the impact on the physical stability of APAP. The lowest levels of APAP precipitation were observed for fill material compositions including increased amounts of povidone K-30 and propylene glycol, and decreased amounts of plasticizers in the softgel shell.

Example 1B—Chemical Stability: In addition to the physical stability of the fill material compositions, described above, fill material compositions encapsulated in a conventional softgel shell were also evaluated for chemical stability under accelerated conditions. The chemical stability of fill material compositions observed under accelerated conditions showed an unsuitably high amount of PE degradation for all compositions encapsulated in conventional softgel shells. For example, some results showed a loss in PE of as much as 7-10% over a period of two months.

Additionally, as the PE degradation increased, the appearance of unknown degradants in the fill material also increased. To determine the identity of these unknown degradants, fill material composition material was encapsulated, stressed at 70° C., and assayed over time. The resulting chromatograms, provided in FIG. 1, were compared to determine the identity of a peak that increased as the amount of PE decreased (i.e., as a result of PE instability).

FIG. 1 shows four overlapping chromatograms of a fill material composition stressed at 70° C. according to some embodiments described above. Specifically, the chromatograms were obtained at 0, 5, 13, and 22 days to observe the effects of the fill material composition over time. As shown in the Figure, the overlapping chromatograms demonstrate a progressively increasing peak over time (at approximately 21.6 minutes).

An evaluation of each of the fill material components, in light of the increasing peak of FIG. 1, revealed that the peak corresponded to the retention time of povidone K-30. Additionally, as the peak increased in size, an ultraviolet (UV) maximum at −276 nm manifests, indicating a likelihood that the unknown degradant represented by the increasing peak in FIG. 1 is directly related to PE degradation (explained in further detail below).

Example 2—Identifying Causes of PE Instability: To confirm that the increasing peak in FIG. 1 was related to PE degradation, two separate samples of fill material were prepared. Both samples comprised all inactive ingredients included in the compositions of Table 1 (i.e., PEG, propylene glycol, povidone K-30, and water). The first sample additionally included PE (the "PE-only" sample). The second sample, in addition to PEG, propylene glycol, povidone K-30, and water, additionally included APAP, guaifenesin, and dextromethorphan, but no PE. Each sample was tested at 70° C. and analyzed using chromatography at various times over a period of 15 days (depicted in FIG. 2).

Figure 2:
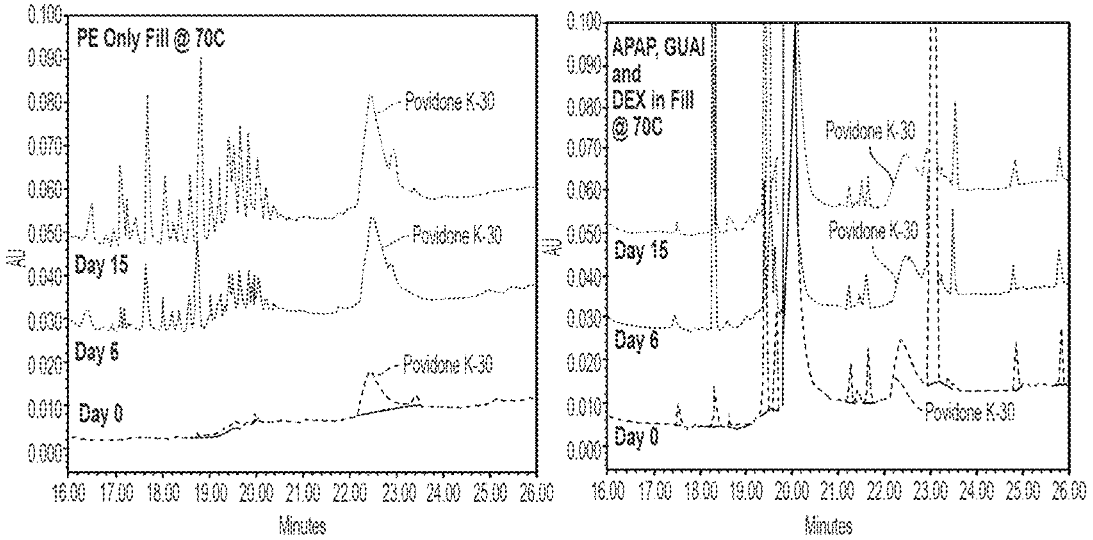
FIG. 2 shows a change in povidone K-30 in the presence of PE according to some embodiments.

FIG. 2 shows overlapping chromatograms for both samples described above. The PE-only sample is provided on the left-hand side of the Figure, and the APAP, guaifenesin, and dextromethorphan sample with no PE is provided on the right-hand side of the Figure. Chromatograms were obtained at 0, 6, and 15 days. FIG. 2 demonstrates that the peak at approximately 21.6 minutes only increased for the first sample comprising PE. In contrast, the peak remains at approximately the same height for the sample including APAP, guaifenesin, and dextromethorphan, but no PE. Accordingly, the chromatograms of FIG. 2 confirm that the unknown degradant, represented by the 21.6-minute peak, resulted from interactions between PE and povidone K-30.

Figure 3:
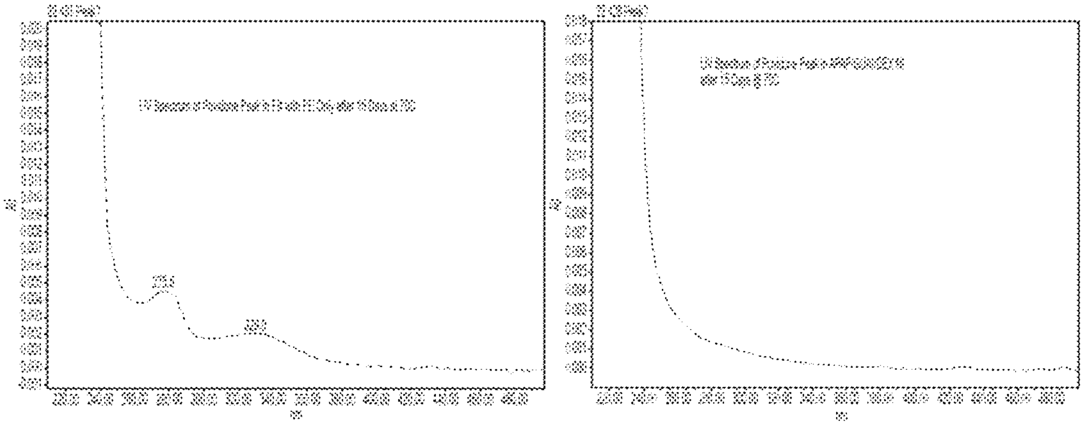
FIG. 3 shows a change in the povidone K-30 spectrum over time due to the presence of PE, according to some embodiments.

As mentioned above, as the peak increases with size over time, a UV maximum at −276 nm also develops, shown in FIG. 3. The left-hand side of the Figure shows a UV spectrum for a povidone K-30 peak in a fill material composition including only PE (no other APIs). The right-hand side of the Figure shows a UV spectrum for a povidone K-30 peak in a fill material composition including APAP, guaifenesin, and dextromethorphan (but no PE). As depicted in FIG. 3, the UV spectrum of the povidone K-30 peak for fill material compositions comprising PE changed to indicate a UV maximum of about 276 nm. However, the UV spectrum of the povidone K-30 peak remained unchanged for compositions without PE. Accordingly, this data further supports that the observed PE degradation is a result of interactions between povidone K-30 and PE.

Similar tests (to those provided in FIGS. 1-3) were performed on fill material compositions comprising povidone K-12 instead of povidone K-30. However, no interaction was observed between the povidone K-12 and the PE in these tests, suggesting that povidone K-12 does not noticeably contribute to the degradation of PE.

Example 3—Using Antioxidants to Control the Formation of Degradants: Fill material composition samples were prepared with the addition of potassium iodide (KI) to evaluate the effect of both ionic strength and the presence of iodine on the formation of the PE-povidone peak. The results, provided in FIG. 4, indicate that the addition of KI had little effect on the formation of the PE-povidone peak.

Figure 4:
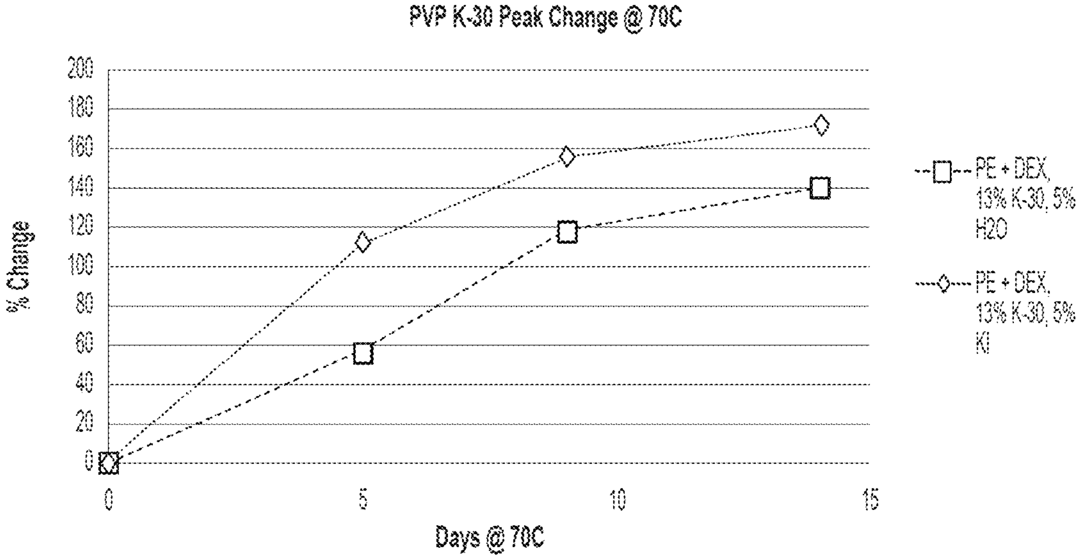
FIG. 4 shows the effect of KI in the fill material composition on the formation of the PE-povidone peak.

Specifically, FIG. 4 shows the results of two different samples of fill material compositions. The two samples each included PE, dextromethorphan, and 13% povidone K-30. Additionally, one sample included 5% KI and one sample included 5% water. Both samples were tested over a period of 15 days at 70° C. and show a relatively large PE-povidone peak formation. Thus, these results indicate that the addition of KI to the fill material composition provided little effect on the formation of the PE-povidone peak as compared to the fill material composition comprising only water and no KI.

Figure 5:
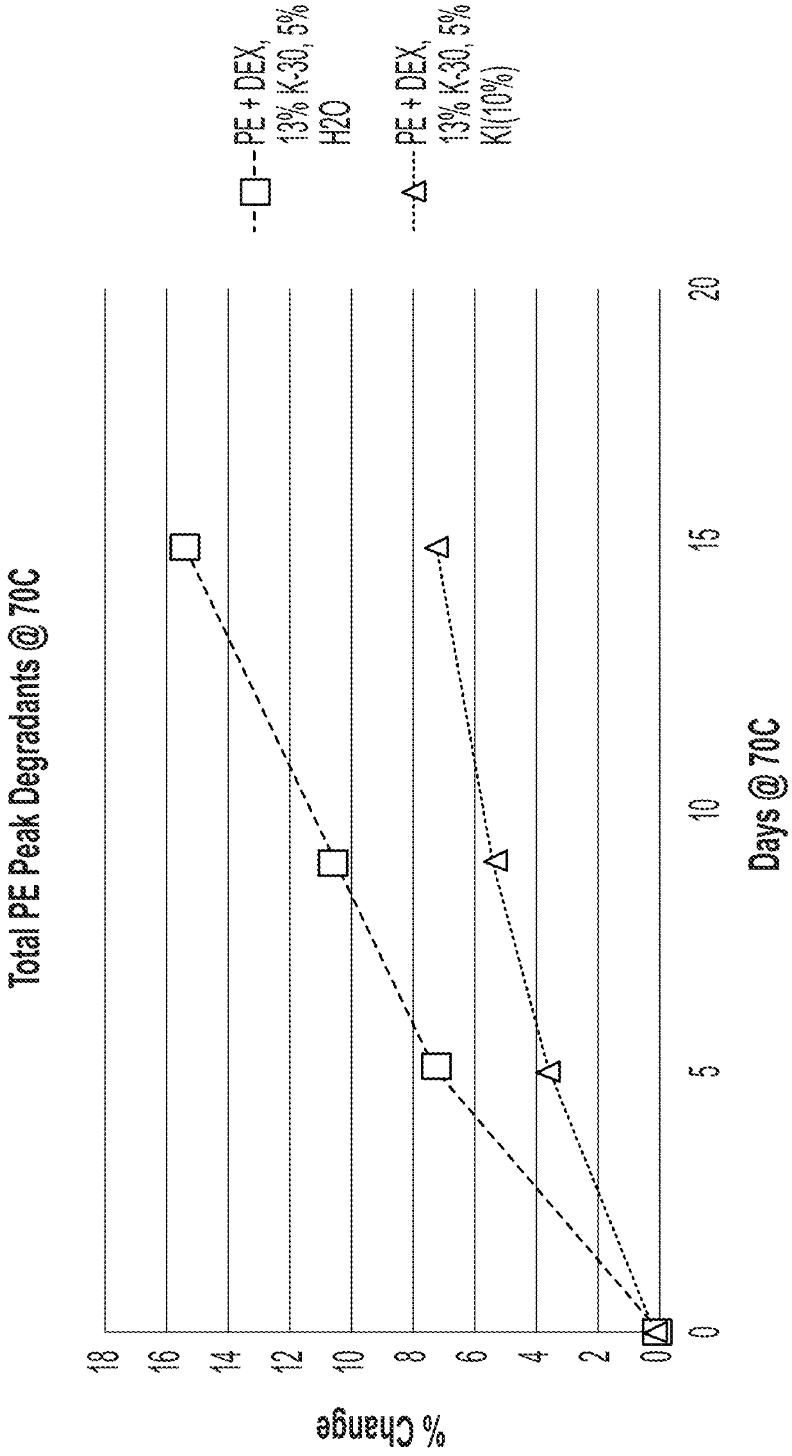
FIG. 5 shows the effect of KI in the fill material composition on the formation of total PE-related degradants according to some embodiments.

Although the addition of KI to the fill material composition had little effect on the formation of the PE-povidone peak, it did have an effect on the formation of other known PE-related substances (shown in FIG. 5). FIG. 5 shows two samples of fill material compositions tested over a period of 15 days at 70° C. Both samples included PE, dextromethorphan, and 13% povidone K-30. One sample included only water, and the other sample included KI. As shown, the fill material composition sample with KI showed less formation of PE degradants than the water-only fill material composition sample.

Accordingly, not only does the presence of an acid improve the stability of an API in a fill material composition of a softgel, but the presence of an antioxidant, such as KI, is also necessary to reduce the presence of certain degradants that may otherwise contribute to the instability of the API.

Example 4—Inhibiting Interactions Between APIs (e.g., Phenylephrine) and Inactive Ingredients: Various studies were conducted to evaluate the effect of pH, air, peroxide, water, and povidone concentration on the formation of the PE (or "PE-PVP", "PE-povidone") degradant. Some results of these tests are provided in FIG. 6.

Figure 6:
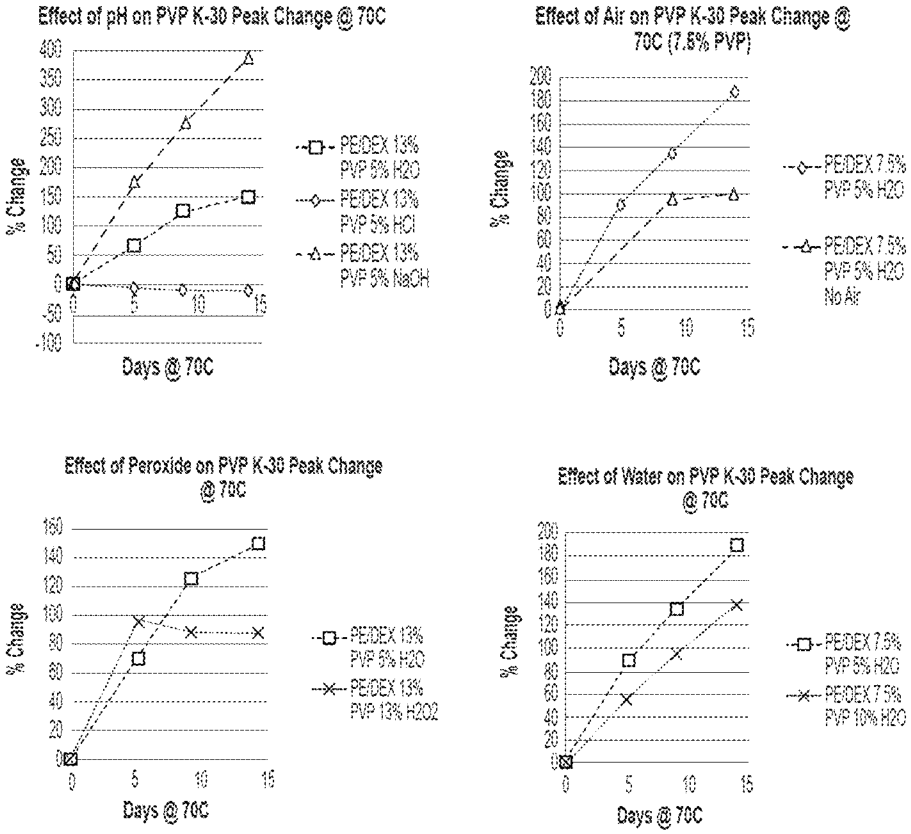
FIG. 6 shows the effects of various conditions on the formation of the PE-povidone peak according to some embodiments.

FIG. 6 provides data showing the effects of pH (top left), air (top right), peroxide (bottom left), and water (bottom right) on the povidone K-30 peak change at 70° C. As shown in the FIG. 6, pH has the greatest impact on the formation of the PE-povidone peak. Specifically, samples of fill material compositions including HCl (acidic pH) caused an almost 400% decrease in the PE-povidone peak change compared to fill material compositions including sodium hydroxide (basic pH). None of the other variables (air, peroxide, and/or water) caused such a dramatic effect on the povidone K-30 peak.

Example 5—Testing the Effects of pH: Once it was determined that pH impacted PE stability, various pH values were tested. Fill material compositions were prepared at various pH values using an acetate buffer were prepared. The samples were tested over a period of 15 days at 70° C., and the results are provided in FIG. 7.

Figure 7:
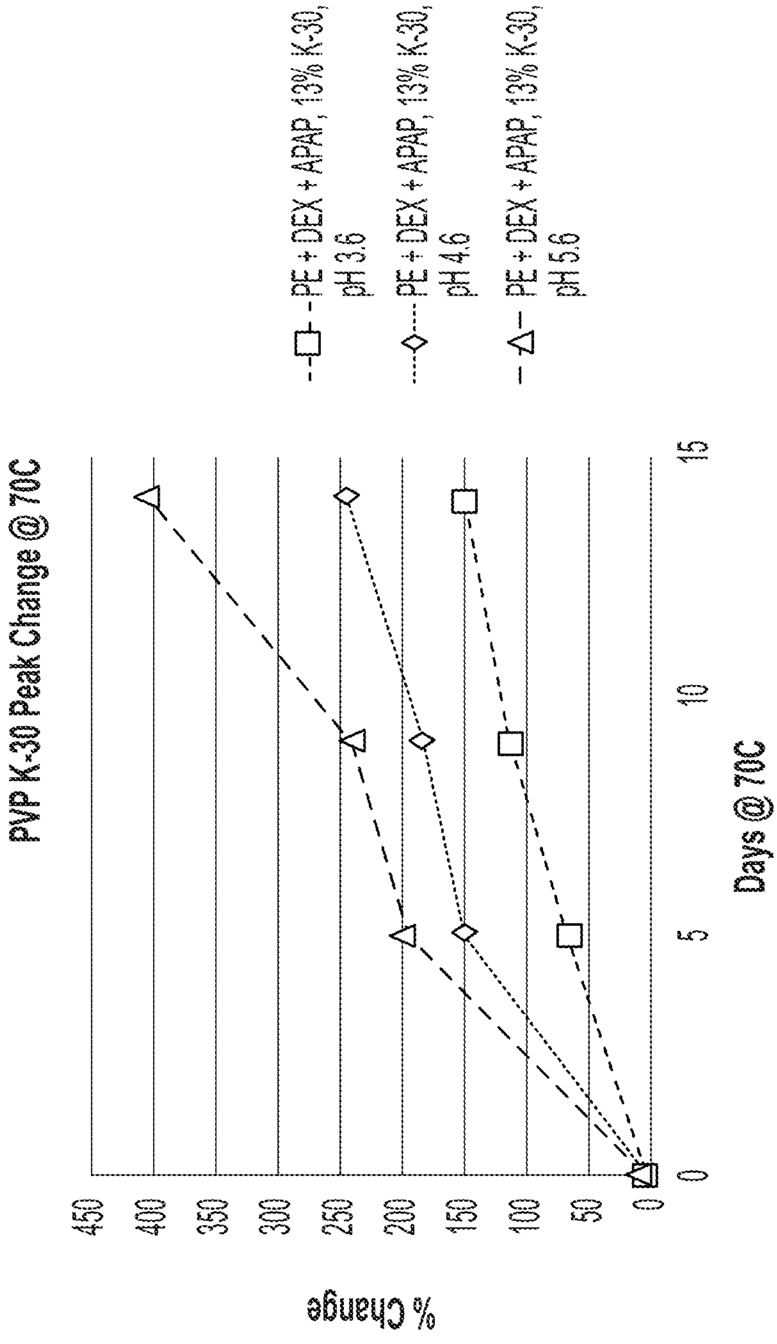
FIG. 7 shows the effect of fill material composition pH on the formation of the PE-povidone peak according to some embodiments.

FIG. 7 provides data from three different fill material compositions. One sample was tested at a pH of 3.6, one sample was tested at a pH of 4.6, and one sample was tested at a pH of 5.6. Based on the results provided in the Figure, the PE-povidone peak is directly proportional to the pH of the fill material composition. In particular, as the pH of the fill material composition decreases, the interaction between the povidone and the PE also decreases.

Example 6—Adding Acid to the Fill Material Composition: The results of the tests depicted in FIG. 7 shows that lowering the acidity of the fill material composition can lower the degradation of the PE. To lower the acidity of the fill material composition, various amounts of 0.1 N HCl were added to the fill material composition and tested.

The various fill material composition samples prepared with various amounts of HCl were stressed at 70° C. and tested over a period of 15 days. In particular, five different samples were prepared and tested over a period of 15 days. All of the samples included PE, dextromethorphan, and 13% povidone K-30. However, the five samples comprised various amounts of HCl: 5% 1.0N HCl, 3.75% 1.0N HCl, 2.5% 1.0N HCl, 0.5% 1.0N HCl, and 5% water (no HCl). The results of these tests are provided in FIG. 8 and described below.

Figure 8:
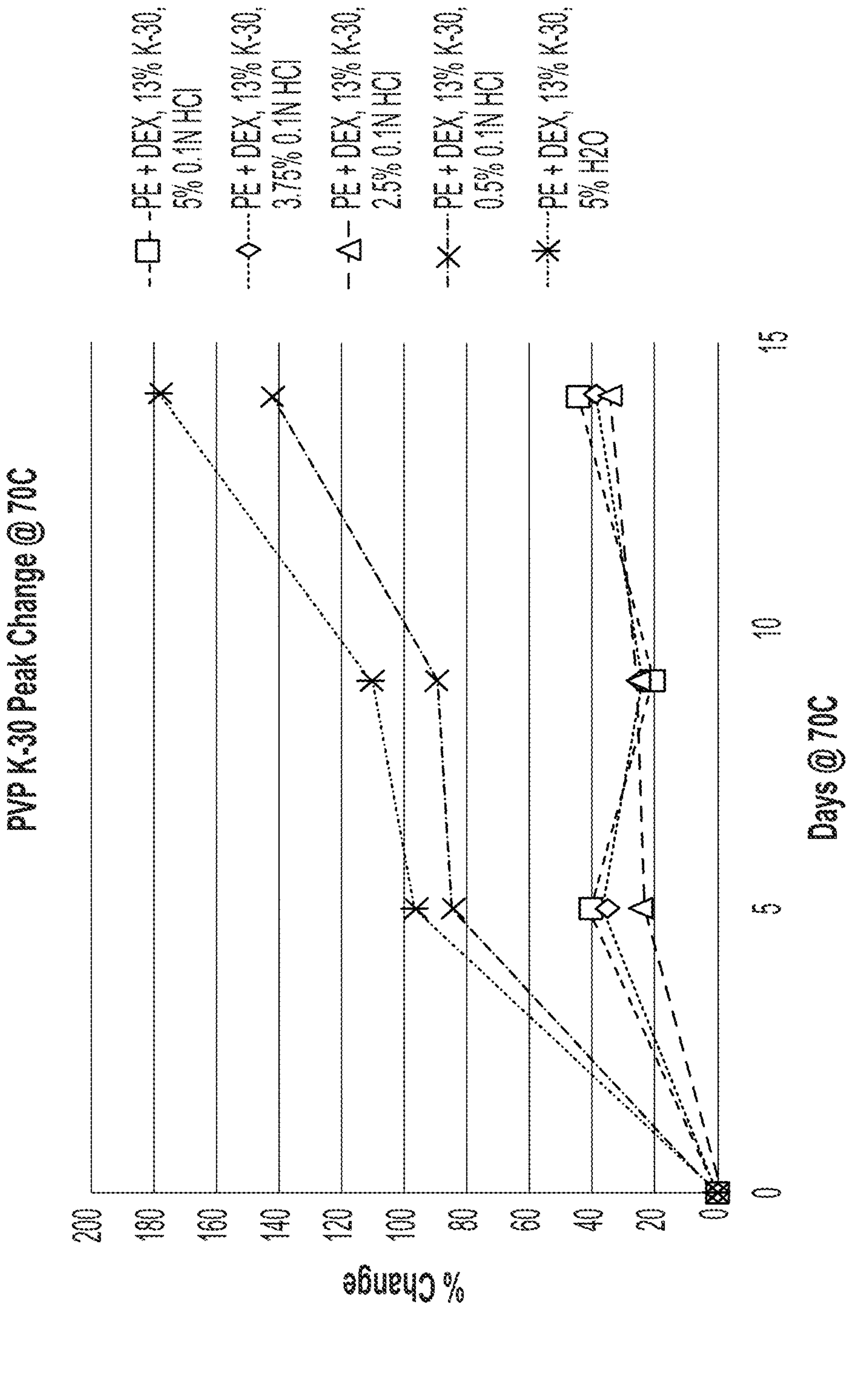
FIG. 8 shows the effect of various concentrations of HCl on the formation of the PE-povidone peak according to some embodiments.

As shown in FIG. 8, the fill material composition including only water (at approximately a neutral pH) exhibited the highest effect on the povidone K-30 peak. In contrast, the fill material composition including 0.5% 0.1N HCl showed slightly less of an effect on the povidone K-30 peak, and the fill material composition samples comprising 2.5%, 3.75%, and 5.0% 0.1N HCl showed a significantly less impact on the povidone K-30 peak.

Examples 7-9—PE Stability of Fill Material Compositions Comprising Acid and Antioxidants: To monitor and evaluate the formation of all PE degradants, fill material composition additives were evaluated using fill material compositions including only the APIs PE and dextromethorphan. Various amounts of HCl and KI were tested with fill material composition A of Table 1, in addition to various antioxidants, in order to monitor the effect on all APIs present in combination. Composition A was also used because it showed the lowest amount of APAP precipitation (described above).

These trials confirm that the stability of PE is the greatest in the presence of HCl. However, the high acidity of the composition due to the addition of the HCl increases the formation of both 4-aminophenol and PE-RS-1 (other PE-related degradants). Thus, the addition of KI as an antioxidant is needed to help control the level of these other degradants, described above. The addition of other antioxidants showed little effect on the stability of the composition. The results of this study are provided in FIGS. 9-11 and described below.

Figure 9:
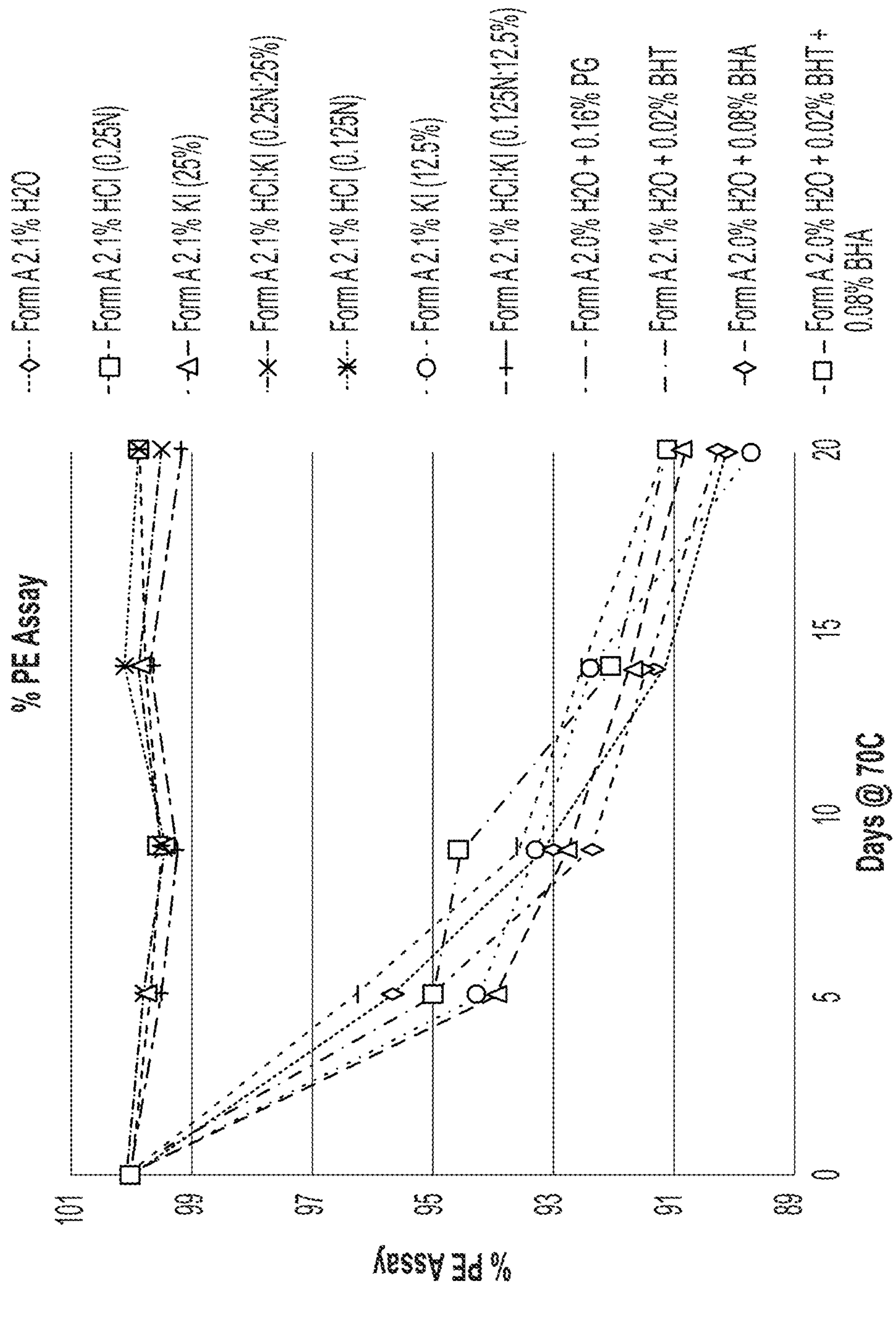
FIG. 9 shows the effects of HCl, KI, and additional antioxidants on the stability of PE in a fill material composition according to some embodiments.

FIG. 9 shows the effect of HCl, KI, and additional antioxidants on the stability of PE in fill material composition according to some embodiments. Specifically, eleven different samples were tested over a period of 20 days at 70° C. The fill material composition samples included a fill material composition comprising one of the following: 2.1% water; 2.1% HCl (0.25N); 2.1% KI (25%); 2.1% HCl:KI (0.25N:25%); 2.1% HCl (0.125N); 2.1% KI (12.5%); 2.1% HCl:KI (0.125N:12.5%); 2.0% water and 0.16% propyl gallate (PG); 2.1% water and 0.02% butylated hydroxytoluene (BHT); 2.0% water and 0.08% butylated hydroxyanisole (BHA); or 2.0% water and 0.02% BHT and 0.08% BHA.

Only the samples comprising HCl exhibited suitable PE stability by maintaining at least 99 percent of the original amount of PE over the course of the trial. In contrast, the samples without HCl exhibited insufficient PE stability by losing at least eight percent of the original amount of PE over the course of the 20-day testing period. These results confirm that a fill material composition comprising a lower pH can help minimize PE degradation in a softgel.

Figure 10:
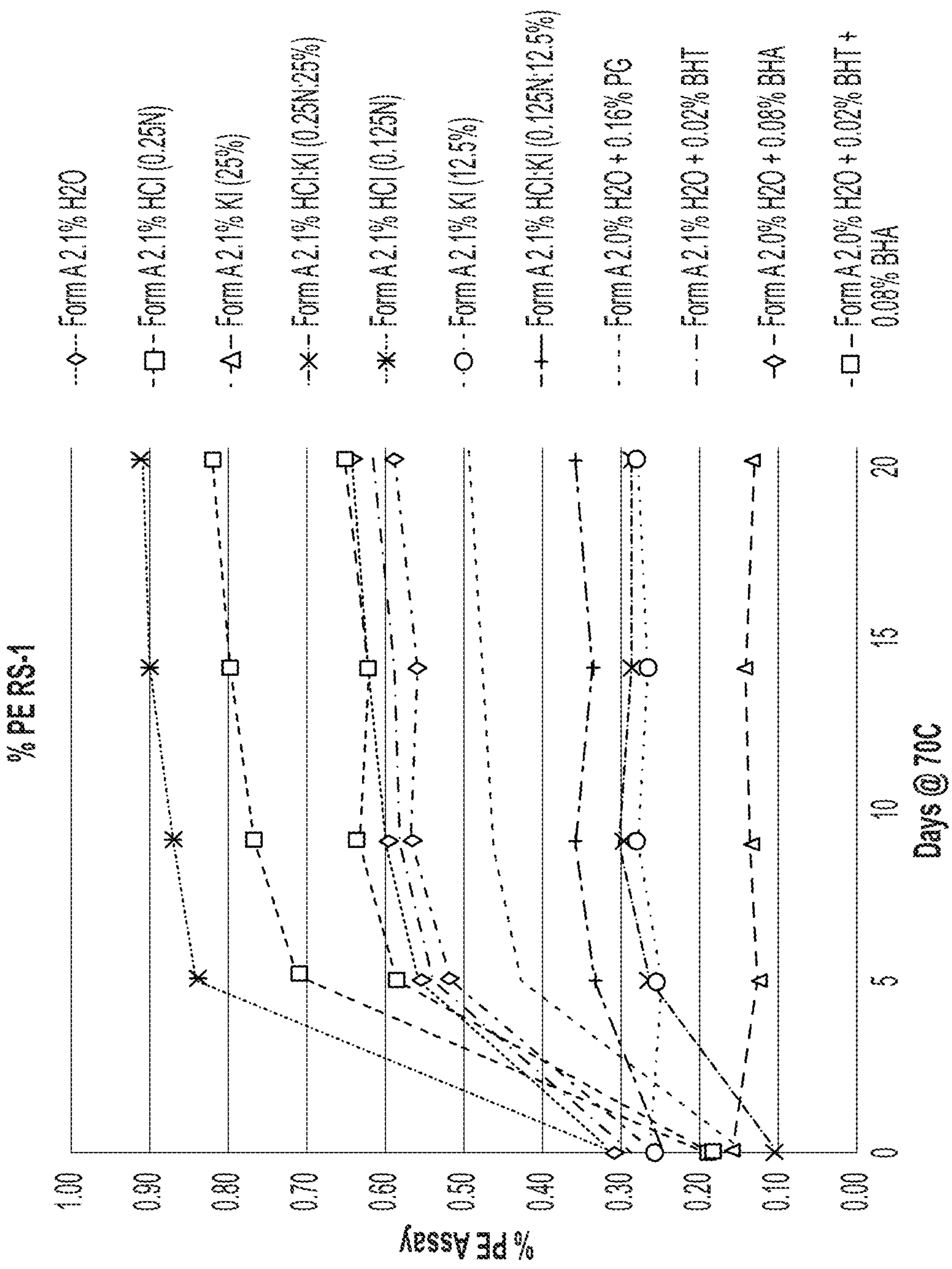
FIG. 10 shows the effect of HCl, KI, and additional antioxidants on the formation of PE RS-1 in fill material compositions according to some embodiments.

FIG. 10 shows the effects of HCl, KI, and additional antioxidants on the formation of PE RS-1 in a fill material composition according to some embodiments. PE RS-1 is a degradant of PE. Thus, increasing levels of PE RS-1 indicate increasing levels of PE degradation. The 11 samples tested in this study were the same as those tested in FIG. 9. The 11 samples were tested over a period of 20 days at 70° C. Specifically, the fill material composition samples included a fill material composition comprising one of the following: 2.1% water; 2.1% HCl (0.25N); 2.1% KI (25%); 2.1% HCl:KI (0.25N:25%); 2.1% HCl (0.125N); 2.1% KI (12.5%); 2.1% HCl:KI (0.125N:12.5%); 2.0% water and 0.16% propyl gallate (PG); 2.1% water and 0.02% butylated hydroxytoluene (BHT); 2.0% water and 0.08% butylated hydroxyanisole (BHA); or 2.0% water and 0.02% BHT and 0.08% BHA.

The results of FIG. 10 show that PE RS-1 levels increase in fill material compositions comprising only HCl. However, in fill material compositions comprising KI (with or without HCl), the levels of PE RS-1 levels remain relatively low. Thus, this study confirms that the presence of KI in the fill material composition can help control the generation of PE RS-1, an undesirable PE degradant.

Figure 11:
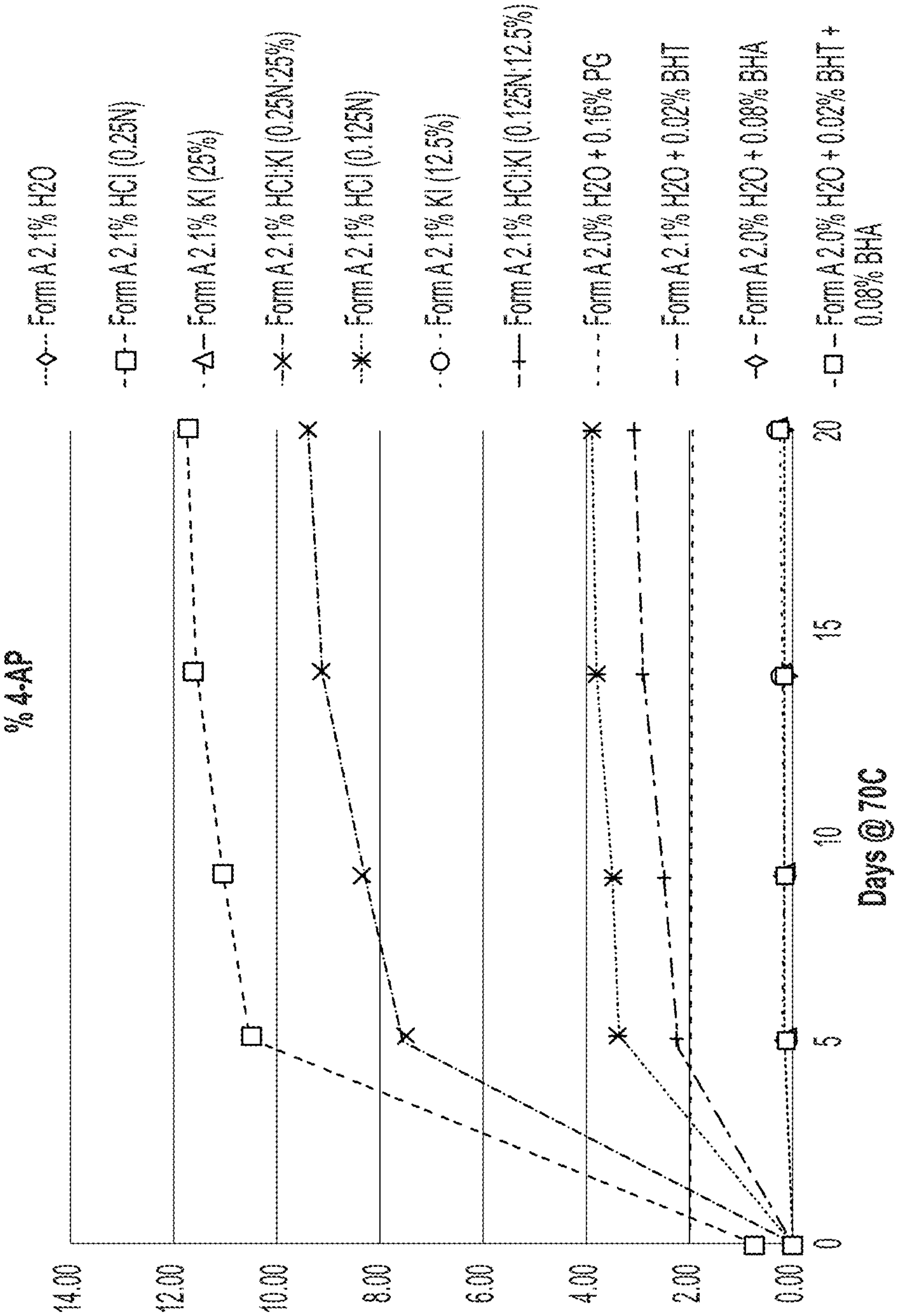
FIG. 11 shows the effects of HCl, KI, and additional antioxidants on the formation of 4-aminophenol in fill material compositions according to some embodiments.

FIG. 11 provides the effects of HCl, KI, and additional antioxidants on the formation of 4-aminophenol in fill material compositions according to some embodiments. 4-aminophenol is another example of a PE degradant. The 11 samples were the same as those tested in FIGS. 9 and 10. Specifically, the fill material composition samples included a fill material composition comprising one of the following: 2.1% water; 2.1% HCl (0.25N); 2.1% KI (25%); 2.1% HCl:KI (0.25N:25%); 2.1% HCl (0.125N); 2.1% KI (12.5%); 2.1% HCl:KI (0.125N:12.5%); 2.0% water and 0.16% propyl gallate; 2.1% water and 0.02% butylated hydroxytoluene (BHT); 2.0% water and 0.08% butylated hydroxyanisole (BHA); or 2.0% water and 0.02% BHT and 0.08% BHA.

Based on the results provided in FIG. 11, the formation of 4-aminophenol increases with compositions comprising HCl and not KI. However, the level of 4-aminophenol remains lower in compositions having a higher pH and comprising KI. Thus, like the PE RS-1 in FIG. 10, the presence of KI may help control the generation of 4-aminophenol as well as PE RS-1.

Example 10—Encapsulating Fill Materials: Fill material compositions according to various embodiments were encapsulated using Type A (pork skin) and Type B (animal bone) gelatin. The fill material compositions encapsulated with these softgel shells correspond to the embodiments described above. In particular, fill material compositions that exhibited suitable API stability with the presence of HCl and KI were tested in some embodiments. The various softgel samples were tested at both room temperature and under accelerated conditions (50° C. and 70° C.). Additionally, the softgel samples stressed at 50° C. were tested two different ways: stressed when intact and stressed when cut open to allow for air exposure. In some embodiments, fill material composition that was stressed at 70° C. prior to encapsulation was also used.

Figure 12:
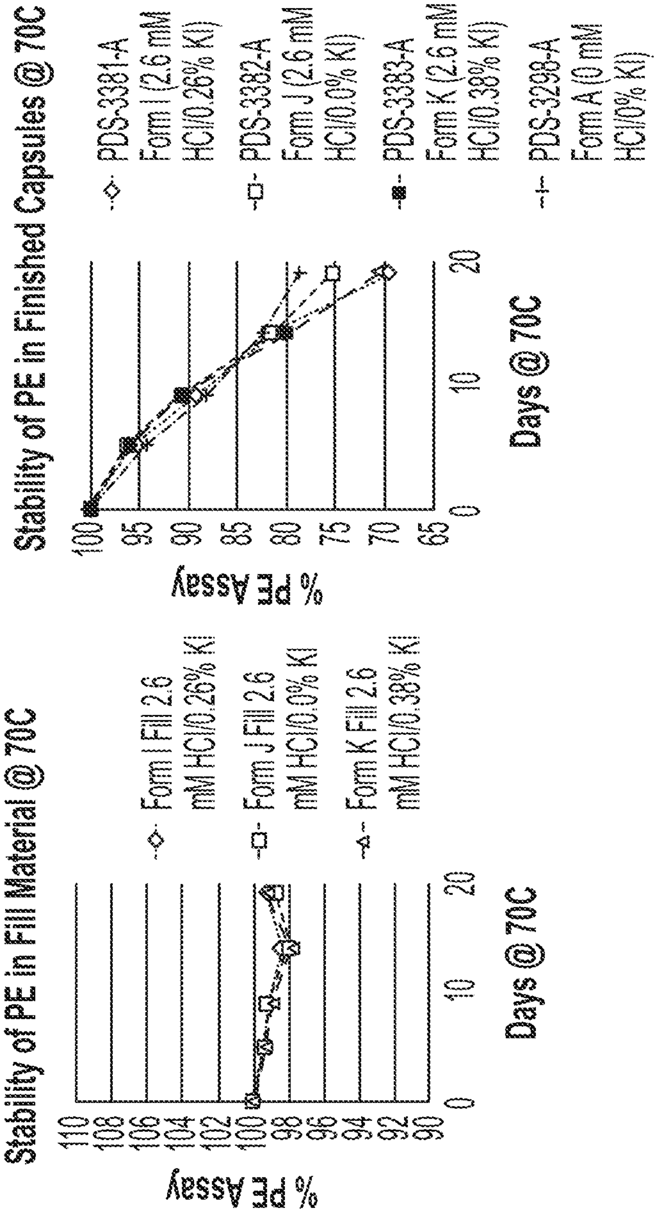
FIG. 12 shows the effect of encapsulation on PE stability for fill material compositions including HCl and KI according to some embodiments.

FIG. 12 demonstrates that softgels stressed at 70° C. experienced rapid PE degradation, regardless of the type of fill material composition. FIG. 12 provides data for the stability of PE in fill material composition tested over a period of 20 days at 70° C. (left-hand side) and data for the stability of PE in finished softgels tested over a period of 20 days at 70° C. (right-hand side). As shown in the left-hand side graph, three different fill material composition samples were tested: one including 2.6 mM HCl/0.26% KI; one including 2.6 mM HCl (0% KI); and one including 2.6 mM HCl/0.38% KI. The PE stability for each of the three samples was almost identical. This data supports the above testing, which identified that PE stability is pH dependent (and inversely proportional with pH). Further, the PE stability of fill material composition (unencapsulated) is not dependent upon the presence of KI.

On the right-hand side of FIG. 12, four different softgel samples were tested: one including a fill material composition comprising 2.6 mM HCl/0.26% KI; one including a fill material composition comprising 2.6 mM HCl (no KI); one including a fill material composition comprising 2.6 mM HCl/0.38% KI; and one including a fill material composition comprising no HCL or KI. All four samples experienced significant PE degradation. Interestingly, the two samples including KI experienced slightly worse PE stability than the two samples not including KI.

Thus, the results in FIG. 12 demonstrate that fill material compositions including HCl and KI experience significant PE degradation upon encapsulation, even though such compositions demonstrated excellent stability prior to encapsulation, as discussed above. Accordingly, the results provided in FIG. 12 indicate that encapsulation of the fill material composition alters the fill material composition in some way, causing PE instability/degradation.

Examples 11-13—Investigating Causes of PE Degradation Upon Encapsulation: Based on the nature of the encapsulation process and the chemical components involved, there are three major factors which can potentially cause PE degradation as a result of encapsulation—influx of water from the shell into the fill material composition, air exposure of the fill material composition, and migration of components into the softgel shell from the fill material composition. Each of these possible causes were tested, the details of which are provided below.

Figure 13:
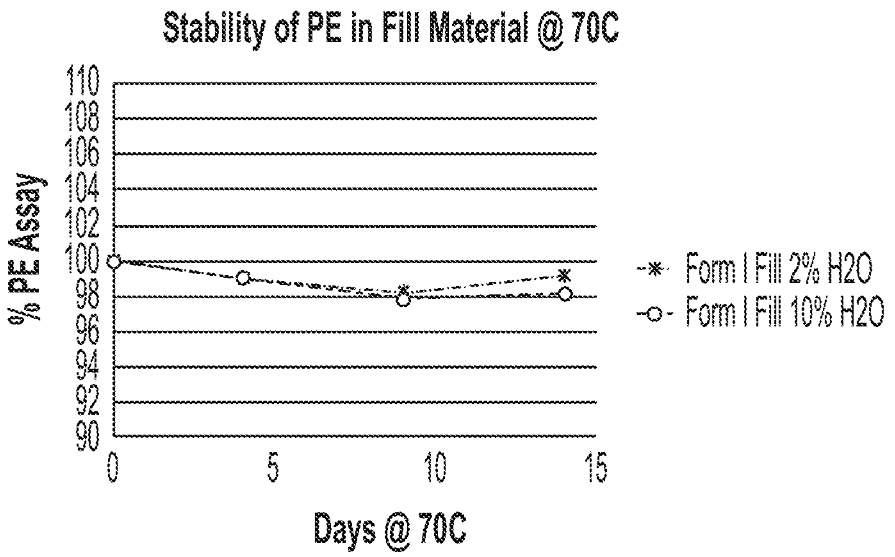
FIG. 13 shows the effects of moisture in the fill material composition on the degradation of PE according to some embodiments.

The first possible cause, influx of water from the softgel shell into the fill material composition, was investigated by increasing the moisture content of the fill material composition and stressing at 70° C. FIG. 13 shows the effect of fill material composition moisture on the degradation of PE. Specifically, two different samples of fill material composition were tested—one including 2% water and the other including 10% water. Both samples were tested over a period of 15 days at 70° C. As shown, the results in FIG. 13 indicate that PE stability is independent from the moisture content of the fill material composition, since there is little distinction in PE stability between the two samples.

Figure 14:
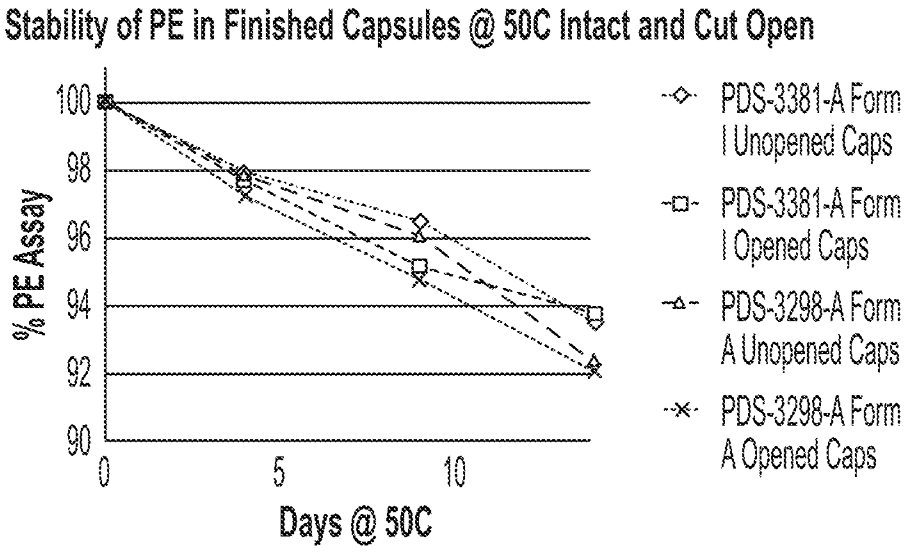
FIG. 14 provides the effect of air exposure on the degradation of PE for softgels with and without HCl and KI according to some embodiments.

The second possible cause, air exposure of the fill material composition, was investigated by stressing both intact and cut open softgels at 50° C. Specifically, FIG. 14 shows the effect of air exposure on the degradation of PE for softgels with and without HCl and KI. Four different softgels were tested: fill material composition without HCl/KI from unopened softgels; fill material composition without HCl/KI from opened softgels; fill material composition with HCl and KI from unopened softgels; and fill material composition with HCl and KI from opened softgels. The results of this investigation are provided in FIG. 14 and demonstrate that there is no obvious correlation between PE stability and air exposure. Further, this investigation shows that the degradation rate of softgels comprising HCl and KI is substantially the same as softgels not comprising HCl or KI.

The third possible cause, migration of fill material composition components into the softgel shell, was investigated by looking at specifically the migration of HCl from the fill material composition into the softgel shell. It is known that hydrophilic components such as acids can rapidly migrate into softgel shells. Further, based on the investigations discussed above, it is also known that the degradation of PE is independent of KI. Note that the migration of other APIs and inactive ingredients was not considered since the degradation rate of PE in fill material compositions not containing HCl and KI is the same prior to encapsulation as compared to the degradation rate of PE in fill material compositions not containing HCl and KI after encapsulation (in finished softgels).

Accordingly, the investigation of the migration of HCl from the fill material composition components into the softgel shell and its effect on the degradation of PE was conducted by comparing the pH of the fill material composition prior to encapsulation and to the pH of the fill material composition after encapsulation (once removed from the softgel shell). Testing showed that the pH of the fill material composition increased approximately 2 full units. (See Examples for more details.) Further, the largest degradant observed in the fill material composition (with HCl and KI) after encapsulation was the PE-formic conjugate. However, the results show that if the pH of the fill material composition is kept below the pKa of the degradant (formic acid), the stability of PE is improved. Accordingly, because the pKa of formic acid is approximately 3.75, the results indicate that the pH of the fill material composition should be controlled to a level below 3.75 to improve PE stability.

Examples 14 & 15: Controlling the pH of the Fill Material Composition Below the pKa of Degradants: In light of the above results, various testing was conducted to control the pH of the fill material composition and study the impact of various pH levels on PE stability. To stabilize the fill material composition pH, various buffers at different pH values from 2.4 to 4.4 and at concentrations of 25 mM and 50 mM were added to fill material compositions not comprising HCl or KI and tested. All samples in FIGS. 15 and 16 were tested over a period of 15 days at 70° C.

Figure 15:
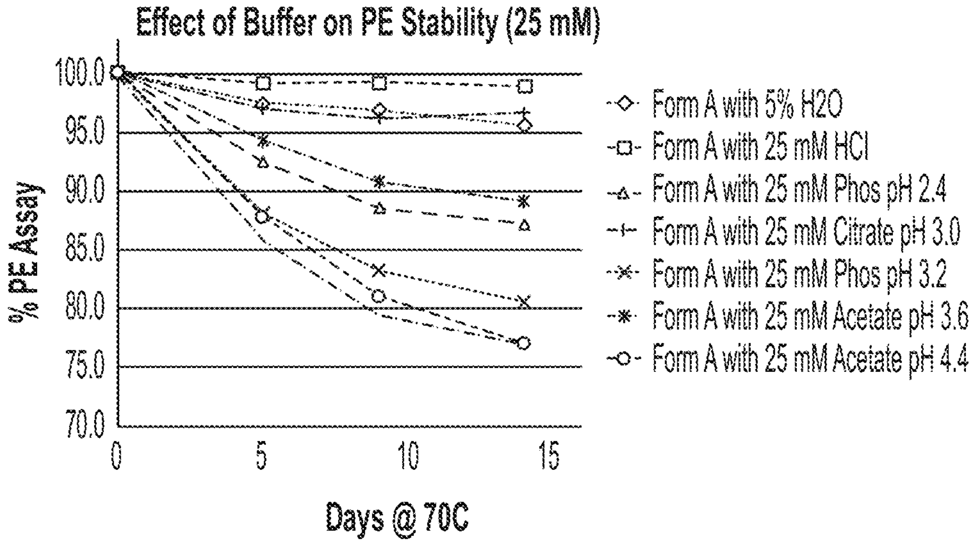
FIG. 15 shows an analysis of buffered fill material compositions at 25 mM according to some embodiments.

FIG. 15 provides a comparison of buffered fill material compositions at various pH values at 25 mM. Specifically, seven different fill material composition samples were tested, including: 5% water; 25 mM HCl; 25 mM phosphate (pH 2.4); 25 mM citrate (pH 3.0); 25 mM phosphate (pH 3.2); 25 mM acetate (pH 3.6); and 25 mM acetate (pH 4.4). As shown in the Figure, the results varied significantly. However, none of the buffers performed as well as HCl in relation to the PE stability.

Figure 16:
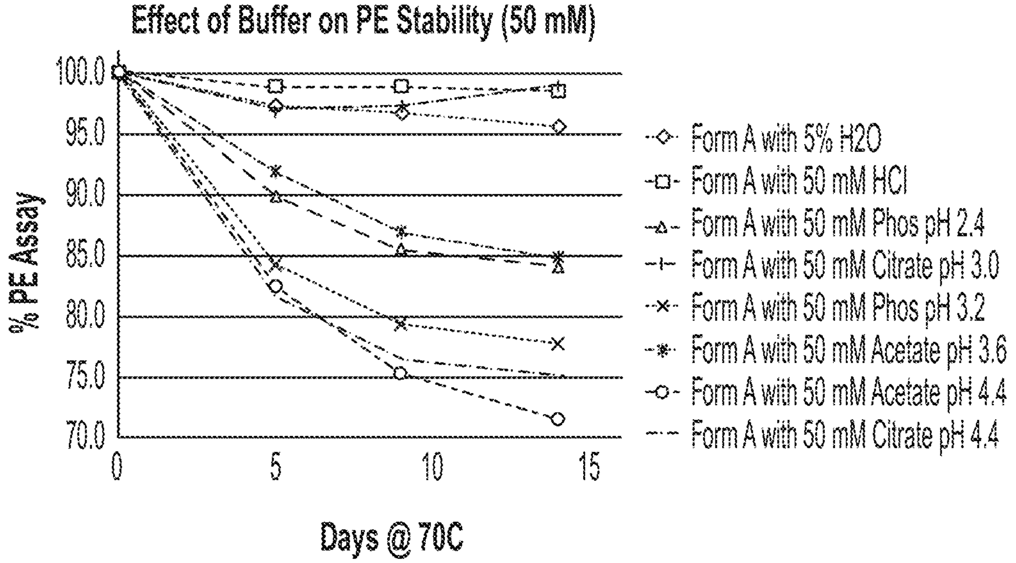
FIG. 16 shows a comparison of buffered fill material compositions at 50 mM according to some embodiments.

FIG. 16 shows a comparison of buffered fill material composition at various pH values at 50 mM. This time, eight different fill material composition samples were tested, including: 5% water; 50 mM HCl; 50 mM phosphate (pH 2.4); 50 mM citrate (pH 3.0); 50 mM phosphate (pH 3.2); 50 mM acetate (pH 3.6); and 50 mM acetate (pH 4.4); and 50 mM citrate (pH 4.4). As with the results of FIG. 15, above, the results here are varied. However, although HCl had the best effect on PE stability, as with the study of FIG. 15, 50 mM citrate also showed suitable results.

Accordingly, introducing various acidic solutions into the fill material composition can improve the stability of the APIs in the softgel. However, the key is to maintain the pH of the fill material composition below the pKa of the degradants of the inactive ingredients that may interact with one or more APIs. In particular, it has been found that adding HCl and KI to the fill material composition of a softgel can improve the stability of APIs such as PE in the softgel. Maintaining the pH of the fill material below the pKa of the PEG and/or povidone degradants can inhibit interactions between the PEG and/or povidone degradants and the API, thus improving the stability of the API(s).

Example 16—Migration of Acid from Conventional Softgel Shell to Fill Material: As described above and depicted in FIGS. 15 and 16, it is likely that encapsulated samples experienced a migration of HCl from the fill material to the softgel shell under certain circumstances. Accordingly, the pH of fill material compositions was compared before and after encapsulation to quantify the severity of this HCl migration. The details of this trial are provided below in Table 2. The pH values of two different fill material compositions are provided—one without HCl or KI, and one with HCl.

| Composition | pH Before Encapsulation | pH After Encapsulation |
|---|---|---|
| Fill material composition Without HCl or KI | 4.6 | N/A |
| Fill material composition With HCl | 3.6 | 5.6 |

Figure 17:
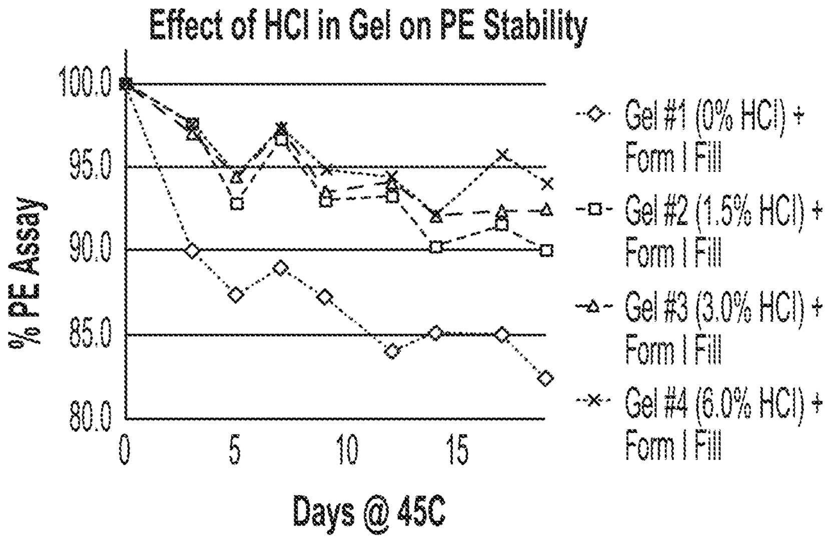
FIG. 17 shows the effects of various levels of HCl in gelatin on PE stability according to some embodiments.

Example 17—Migration of Acid from Softgel Shell Comprising Acidic Solution to Fill Material: The effects of pH equilibrium on controlling the pH of the fill material composition were evaluated with four separate fill material compositions, each containing 0, 3.75, 7.5, or 15 mM of HCl. Each of the four samples was dispensed into a 20 mL vial (approximately 2 g into each vial) and allowed to set and dry. Approximately 5 g of a fill material composition (containing both HCL and KI) was added on top of the gel mix in the vial, and all vials were placed in a water bath at 45° C. The vials were analyzed at predetermined times, the results of which are provided in FIG. 17. As shown in the Figure, the PE degradation of each sample directly correlates to the amount of acid in the gelatin. Specifically, the more HCl present in the gelatin of the gelatin mix, the better the PE stability of the fill material composition on top of the gel mix. Further, the pH of the fill material composition in the vials is inversely proportional to the level of HCl in the gel.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The invention claimed is:

1. A pharmaceutical softgel comprising:

a fill material composition comprising:

15 to 70 wt. % of an active pharmaceutical ingredient (API), wherein the API is selected from the group consisting of ibuprofen, phenylephrine, dextromethorphan, acetaminophen, guaifenesin, and combinations thereof;

2 to 15 wt. % povidone;

0.25 to 5 wt. % potassium iodide;

30 to 60 wt. % polyethylene glycol;

0.5 to 8 wt. % hydrochloric acid; and 0.5 to 5 wt. % propylene glycol, wherein the fill material composition has a pH of 3.75 or less, and a softgel shell.

2. The softgel of claim 1, wherein the softgel shell comprises hydrochloric acid.

3. The softgel of claim 1, wherein the API is phenylephrine.

4. The softgel of claim 1, wherein the fill material composition comprises 30-60 wt. % total API.

5. The softgel of claim 1, wherein the povidone comprises povidone K-30 and the polyethylene glycol comprises PEG 400.

6. The softgel of claim 1, comprising from 1 wt. % to 2 wt. % of 25% potassium iodide.

7. A fill material composition for a softgel comprising:

15 to 70 wt. % of an active pharmaceutical ingredient (API), wherein the API is selected from the group consisting of ibuprofen, phenylephrine, dextromethorphan, acetaminophen, guaifenesin, and combinations thereof;

2 to 15 wt. % povidone, 0.25 to 5 wt. % potassium iodide, 30 to 60 wt. % polyethylene glycol, 0.5 to 8 wt. % hydrochloric acid; and 0.5 to 5 wt. % propylene glycol, wherein the fill material composition has a pH of 3.75 or less.

8. The composition of claim 7, wherein the API is phenylephrine.

9. The composition of claim 7, comprising 30-60 wt. % API.

10. The composition of claim 7, wherein the povidone comprises povidone K-30 and the polyethylene glycol comprises PEG 400.

11. A method of preparing a softgel comprising:

combining 30 to 60 wt. % polyethylene glycol, 0.5 to 5 wt. % propylene glycol, 2 to 15 wt. % povidone, 0.25 to 5 wt. % potassium iodide, 15 to 70 wt. % of an active pharmaceutical ingredient (API), and 0.5 to 8 wt. % an acidic component comprising citric acid, formic acid, acetic acid, and/or hydrochloric acid to form a fill material comprising a pH of 3.75 or less, wherein the API is selected from the group consisting of ibuprofen, phenylephrine, dextromethorphan, acetaminophen, guaifenesin, and combinations thereof; and encapsulating the fill material in a softgel shell to form a softgel.

12. The method of claim 11, wherein the softgel shell comprises hydrochloric acid.

13. The method of claim 11, wherein the API is phenylephrine.

14. The method of claim 11, comprising 30-60 wt. % API.

15. The method of claim 11, wherein the povidone comprises povidone K-30 and the polyethylene glycol comprises PEG 400.

16. The method of claim 11, wherein adding an acid comprises adding 0.5 wt. % to 1.0 wt. % of 0.5 N hydrochloric acid.

17. The method of claim 11, wherein preparing a fill material composition comprises adding 1 wt. % to 2 wt. % of 25% potassium iodide.

* * * * *